United States Patent
Foschini et al.

(10) Patent No.: US 12,119,115 B2
(45) Date of Patent: Oct. 15, 2024

(54) SYSTEMS AND METHODS FOR SELF-SUPERVISED LEARNING BASED ON NATURALLY-OCCURRING PATTERNS OF MISSING DATA

(71) Applicant: Evidation Health, Inc., San Mateo, CA (US)

(72) Inventors: Luca Foschini, Santa Barbara, CA (US); Filip Jankovic, Santa Barbara, CA (US); Raghunandan Melkote Kainkaryam, Cincinnati, OH (US); Juan Ignacio Oguiza Mendez, Valencia (ES); Arinbjörn Kolbeinsson, Berlin (DE)

(73) Assignee: Evidation Health, Inc., San Mateo, CA (US)

( * ) Notice: Subject to any disclaimer, the term of this patent is extended or adjusted under 35 U.S.C. 154(b) by 0 days.

(21) Appl. No.: 18/156,010

(22) Filed: Jan. 18, 2023

(65) Prior Publication Data
US 2023/0245777 A1   Aug. 3, 2023

Related U.S. Application Data

(60) Provisional application No. 63/412,054, filed on Sep. 30, 2022, provisional application No. 63/306,447, filed on Feb. 3, 2022.

(51) Int. Cl.
*G16H 50/20* (2018.01)
*G16H 50/70* (2018.01)

(52) U.S. Cl.
CPC ............ *G16H 50/20* (2018.01); *G16H 50/70* (2018.01)

(58) Field of Classification Search
CPC ............................... G16H 50/20; G16H 50/70
See application file for complete search history.

(56) References Cited

U.S. PATENT DOCUMENTS

| | | |
|---|---|---|
| 6,947,953 B2 | 9/2005 | Herzenberg et al. |
| 7,937,461 B2 | 5/2011 | Kutzik et al. |
| (Continued) | | |

FOREIGN PATENT DOCUMENTS

| | | |
|---|---|---|
| IN | 202041010784 | 11/2020 |
| WO | WO-2006031888 A2 | 3/2006 |
| (Continued) | | |

OTHER PUBLICATIONS

Quyyum et al. Secure and Robut Machine Learning for Healthcare: A Survey, IEEE Reviews in Biomedical Engineering, vol. 14, p. 156, 2021.*

(Continued)

*Primary Examiner* — Jay M. Patel
(74) *Attorney, Agent, or Firm* — Wilson Sonsini Goodrich & Rosati

(57) ABSTRACT

Disclosed is a method comprising accessing, by a machine learning system, a set of data records for a plurality of users, the data records representative of physical statistics measured for each of the plurality of users over a time period. At least a subset of the data records comprises patterns of missing data for at least a portion of the time period. The method also comprises generating a set of masked data records by masking a subset of the data records in accordance with a pattern of natural missingness from a data record. The method also comprises generating, by the machine learning system, a set of learned representations from at least the set of masked data records. Finally, the method comprises fine tuning, by the machine learning system, a machine learning model using the set of learned representations, the machine learning model configured to perform a downstream machine learning task.

30 Claims, 13 Drawing Sheets

(56) References Cited

U.S. PATENT DOCUMENTS

| | | |
|---|---|---|
| 8,392,215 B2 | 3/2013 | Tawil |
| 8,930,218 B1 | 1/2015 | Oakley et al. |
| 9,710,764 B1 | 7/2017 | Hodjat et al. |
| 9,760,422 B2 | 9/2017 | Chen et al. |
| 10,327,697 B1 | 6/2019 | Stein et al. |
| 10,524,697 B2 | 1/2020 | Gubbi Lakshminarasimha et al. |
| 11,056,242 B1 | 7/2021 | Jain et al. |
| 11,127,506 B1 | 9/2021 | Jain et al. |
| 11,387,000 B2 | 7/2022 | Saliman et al. |
| 11,468,992 B2 | 10/2022 | Pulicharam et al. |
| 11,471,115 B2 | 10/2022 | Rance et al. |
| 2001/0003099 A1 | 6/2001 | Von |
| 2005/0228691 A1 | 10/2005 | Paparo |
| 2006/0084847 A1 | 4/2006 | Reed et al. |
| 2007/0288277 A1 | 12/2007 | Neuhauser et al. |
| 2008/0104167 A1 | 5/2008 | Cohen et al. |
| 2008/0146334 A1 | 6/2008 | Kil |
| 2008/0154707 A1 | 6/2008 | Mittal et al. |
| 2008/0214903 A1 | 9/2008 | Orbach |
| 2008/0319786 A1 | 12/2008 | Stivoric et al. |
| 2009/0006457 A1 | 1/2009 | Stivoric et al. |
| 2009/0055854 A1 | 2/2009 | Wright et al. |
| 2009/0070797 A1 | 3/2009 | Ramaswamy et al. |
| 2009/0138415 A1 | 5/2009 | Lancaster |
| 2009/0299767 A1 | 12/2009 | Michon et al. |
| 2011/0066464 A1 | 3/2011 | George |
| 2011/0184250 A1 | 7/2011 | Schmidt et al. |
| 2012/0046966 A1 | 2/2012 | Chang et al. |
| 2012/0124099 A1 | 5/2012 | Stewart |
| 2012/0246102 A1 | 9/2012 | Sudharsan |
| 2012/0278134 A1 | 11/2012 | Papay et al. |
| 2013/0004473 A1 | 1/2013 | Kochel et al. |
| 2013/0096943 A1 | 4/2013 | Carey et al. |
| 2013/0197894 A1 | 8/2013 | Sablinski |
| 2013/0216989 A1 | 8/2013 | Cuthbert |
| 2014/0005502 A1 | 1/2014 | Klap et al. |
| 2014/0095417 A1 | 4/2014 | Herz et al. |
| 2014/0129247 A1 | 5/2014 | Op Den Buijs et al. |
| 2014/0188512 A1 | 7/2014 | Parker et al. |
| 2014/0229418 A1 | 8/2014 | Graham, II et al. |
| 2014/0278449 A1 | 9/2014 | Kharraz Tavakol |
| 2014/0315168 A1 | 10/2014 | Movellan et al. |
| 2014/0344013 A1 | 11/2014 | Karty et al. |
| 2015/0006456 A1 | 1/2015 | Sudharsan |
| 2015/0163121 A1 | 6/2015 | Mahaffey et al. |
| 2015/0242518 A1 | 8/2015 | Rosenbaum et al. |
| 2015/0243180 A1 | 8/2015 | Kim et al. |
| 2016/0012194 A1 | 1/2016 | Prakash et al. |
| 2016/0089089 A1 | 3/2016 | Kakkar et al. |
| 2016/0142894 A1 | 5/2016 | Papakonstantinou et al. |
| 2016/0283686 A1 | 9/2016 | Hu et al. |
| 2016/0328991 A1 | 11/2016 | Simpson et al. |
| 2016/0357173 A1 | 12/2016 | Foschini et al. |
| 2016/0361020 A1 | 12/2016 | LeBoeuf et al. |
| 2017/0053091 A1 | 2/2017 | Holmes et al. |
| 2017/0140109 A1 | 5/2017 | Kheifetz et al. |
| 2017/0188841 A1 | 7/2017 | Ma et al. |
| 2017/0206795 A1 | 7/2017 | Kaleal, III |
| 2017/0245808 A1 | 8/2017 | Jain et al. |
| 2017/0249434 A1 | 8/2017 | Brunner |
| 2017/0293846 A1* | 10/2017 | Zyglowicz ............... A61B 5/20 |
| 2018/0330824 A1 | 11/2018 | Athey et al. |
| 2018/0338733 A1 | 11/2018 | Jain et al. |
| 2018/0344215 A1 | 12/2018 | Ohnemus et al. |
| 2018/0350451 A1 | 12/2018 | Ohnemus et al. |
| 2019/0019581 A1 | 1/2019 | Vaughan et al. |
| 2019/0043337 A1 | 2/2019 | Liu et al. |
| 2019/0066845 A1 | 2/2019 | Roy et al. |
| 2019/0076031 A1 | 3/2019 | Valys et al. |
| 2019/0209022 A1 | 7/2019 | Sobol et al. |
| 2019/0245824 A1 | 8/2019 | Hiir et al. |
| 2019/0287660 A1 | 9/2019 | Oliveira et al. |
| 2019/0287669 A1* | 9/2019 | Sun ....................... G16H 10/60 |
| 2019/0339291 A1 | 11/2019 | Edmonds et al. |
| 2019/0355472 A1 | 11/2019 | Kutzko |
| 2019/0385711 A1 | 12/2019 | Shriberg et al. |
| 2020/0034585 A1* | 1/2020 | Lu ..................... G06K 19/0723 |
| 2020/0135334 A1 | 4/2020 | Rajasekhar et al. |
| 2020/0161005 A1 | 5/2020 | Lyman et al. |
| 2020/0273578 A1 | 8/2020 | Kutzko et al. |
| 2020/0302775 A1 | 9/2020 | Liu et al. |
| 2020/0372369 A1 | 11/2020 | Gong et al. |
| 2021/0011443 A1 | 1/2021 | Mcnamara et al. |
| 2021/0012902 A1* | 1/2021 | Chawla ............. G06F 18/24133 |
| 2021/0038163 A1 | 2/2021 | Agrawal et al. |
| 2021/0042667 A1 | 2/2021 | Ghosh et al. |
| 2021/0113099 A1* | 4/2021 | Rogers ................. A61B 5/4803 |
| 2021/0117417 A1 | 4/2021 | Hendrickson et al. |
| 2021/0118136 A1 | 4/2021 | Hassan-Shafique et al. |
| 2021/0151194 A1 | 5/2021 | Foschini et al. |
| 2021/0151198 A1 | 5/2021 | Sabeti et al. |
| 2021/0158214 A1 | 5/2021 | Witt et al. |
| 2021/0166803 A1 | 6/2021 | Ellis et al. |
| 2021/0174919 A1 | 6/2021 | Vaughan |
| 2021/0182708 A1 | 6/2021 | Park et al. |
| 2021/0201129 A1* | 7/2021 | Schmude ............... G06N 3/063 |
| 2021/0204914 A1 | 7/2021 | Meral et al. |
| 2021/0241923 A1 | 8/2021 | Foschini et al. |
| 2021/0319887 A1 | 10/2021 | Derrick, Jr. et al. |
| 2022/0068494 A1 | 3/2022 | Op Den Buijs et al. |
| 2022/0343160 A1* | 10/2022 | Park ....................... G06N 3/045 |
| 2023/0033835 A1 | 2/2023 | Rathore et al. |
| 2023/0090138 A1 | 3/2023 | Clay et al. |
| 2023/0187073 A1 | 6/2023 | Foschini et al. |
| 2023/0245777 A1 | 8/2023 | Foschini et al. |
| 2024/0047042 A1 | 2/2024 | Daza |

FOREIGN PATENT DOCUMENTS

| | | |
|---|---|---|
| WO | WO-2014039881 A1 | 3/2014 |
| WO | WO-2019165004 A1 | 8/2019 |
| WO | WO-2021127566 A1 | 6/2021 |
| WO | WO-2021154401 A1 | 8/2021 |
| WO | WO-2021222601 A1 | 11/2021 |
| WO | WO-2022200985 A1 | 9/2022 |
| WO | WO-2023044052 A1 | 3/2023 |
| WO | WO-2023114779 A1 | 6/2023 |
| WO | WO-2023150428 A1 | 8/2023 |

OTHER PUBLICATIONS

PCT/US2022/081465 Invitation to Pay Additional Fees dated Mar. 2, 2023.

U.S. Appl. No. 17/111,765 Non-Final Office Action dated Feb. 17, 2023.

Atito et al.: MC-SSL0.0: Towards Multi-Concept Self-Supervised Learning. arXiv:2111.15340, pp. 1-17 [pre-print] (2021).

Kolbeinsson et al.: Self-supervision of wearable sensors time-series data for influenza detection. arXiv:2112.13755, pp. 1-5 [pre-print] DOI:10.48550/arXiv.2112.13755 [retrieved online Jun. 20, 2023] (2021).

PCT/US2022/081465 International Search Report and Written Opinion dated May 9, 2023.

PCT/US2023/060815 International Search Report and Written Opinion dated Jun. 5, 2023.

Suo et al.: GLIMA: Global and Local Time Series Imputation with Multi-directional Attention Learning. 2020 IEEE International Conference on Big Data (Big Data), Atlanta, GA, USA, pp. 798-807. DOI:10.1109/BigData50022.2020.9378408 (2020).

U.S. Appl. No. 17/946,975 Final Office Action dated May 5, 2023.

U.S. Appl. No. 17/968,413 Final Office Action dated Jun. 7, 2023.

U.S. Appl. No. 16/926,510 Non-Final Office Action dated Jul. 20, 2023.

Althouse et al.: Enhancing disease surveillance with novel data streams: challenges and opportunities. EPJ Data Sci. 4(1):17, pp. 1-8 doi:10.1140/epjds/s13688-015-0054-0 (2015).

Cao et al.: DeepMood: Modeling Mobile Phone Typing Dynamics for Mood Detection. arXiv:1803.08986, pp. 1-9 doi: 10.1145/3097983.3098086 (2018).

Co-pending U.S. Appl. No. 17/111,765, inventors Foschini; Luca et al., filed on Dec. 4, 2020.

(56) References Cited

OTHER PUBLICATIONS

Co-pending U.S. Appl. No. 17/946,975, inventors Clay; Ieuan et al., filed on Sep. 16, 2022.
Co-pending U.S. Appl. No. 17/968,413, inventors Foschini; Luca et al., filed on Oct. 18, 2022.
Co-pending U.S. Appl. No. 18/148,991, inventors Foschini; Luca et al., filed on Dec. 30, 2022.
Daly et al.: Risk stratification and daily symptom monitoring for oncology patients. Journal of Clinical Oncology 37(15)Suppl., p. 6535 DOI:10.1200/JCO.2019.37.15_suppl.6535 (2019).
Element AI: Element AI makes its BAyesian Active Learning library open source. (Retrieved online on Jan. 21, 2021), pp. 1-6 URL: https://www.elementai.cominews/2019/element-ai-makes-its-bayesian-active-learning-library-open-source (2019).
Evidation Health: Achievement. Publication Date Unknown, six pages, [Retrieved online Nov. 4, 2020] URL: https://www.myachievement.com/.
Gal et al.: Bayesian convolutional neural networks with Bernoulli approximate variational inference. ICLR workshop track arXiv:1506.02158, pp. 1-12 doi:10.48550/ARXIV.1506.02158 (2016).
Gal et al.: Deep Bayesian Active Learning with Image Data. arXiv:1703.02910, pp. 1-10 doi:10.48550/ARXIV.1703.02910 (2017).
Gal et al.: Dropout as a Bayesian approximation: Representing model uncertainty in deep learning. International Conference on Machine Learning, pp. 1-10 URL: http://proceedings.mlr.press/v48/gal16.pdf (2016).
Henning: What is Syndromic Surveillance?. MMWR Suppl. 53:5-11 (2004).
Hochreiter et al. Long Short-Term Memory. Neural Computation 9(8):1735-1780 (1997).
Homayounfar et al.: Data mining research trends in computerized patient records. 2011 Federated Conference on Computer Science and Information Systems (FedCSIS), pp. 133-139 (2011).
Houlsby et al.: Bayesian Active Learning for Classification and Preference Learning. arXiv:1112.5745, pp. 1-17 doi:10.48550/ARXIV.1112.5745 (2011).
Li et al.: Digital Health: Tracking Physiomes and Activity Using Wearable Biosensors Reveals Useful Health-Related Information. PLoS Biology, pp. 1-30 DOI:10.1371/journal.pbio.2001402(2017).
Mezlini et al.: Estimating the Burden of Influenza-like Illness on Daily Activity at the Population Scale Using Commercial Wearable Sensors. JAMA Netw Open. 5(5):e2211958:1-12 doi:10.1001/jamanetworkopen.2022.11958 (2022).
Nelson et al.: Continuous, objective measurement of physical activity during chemotherapy for breast cancer: the Activity in Treatment pilot study. Transl Behav Med. 10(4):1031-1038 doi:10.1093/tbm/ibz079 (2020).
Pavel et al.: Behavioral Informatics and Computational Modeling in Support of Proactive Health Management and Care. IEEE Transactions on Biomedical Engineering. 62(12):2763-2775 doi:10.1109/TBME.2015.2484286 (2015).
PCT/US2020/064369 International Search Report and Written Opinion dated Mar. 2, 2021.
PCT/US2022/043874 International Search Report and Written Opinion dated Nov. 17, 2022.
Pentland: Healthwear: medical technology becomes wearable. Computer 37(5), pp. 42-49 doi:10.1109/MC.2004.1297238 (2004).
Radin et al.: Harnessing wearable device data to improve state-level real-time surveillance of influenza-like illness in the USA: a population-based study. Lancet Digit Health 2(2):e85-e93 doi:10.1016/S2589-7500(19)30222-5 (2020).
Schroeder et al.: Examining Self-Tracking by People with Migraine: Goals, Needs, and Opportunities in a Chronic Health Condition. DIS 2018, pp. 135-148 DOI:10.1145/3196709.3196738 (2018).
Simonsen et al.: Infectious Disease Surveillance in the Big Data Era: Towards Faster and Locally Relevant Systems. J Infect Dis. 214(suppl_4):S380-S385 doi:10.1093/infdis/jiw376 (2016).
Turner: New directions in communications (or Which way to the Information Age?). IEEE Communications Magazine 24(10):8-15 doi:10.1109/MCOM.1986.1092946 (1986).
U.S. Appl. No. 14/977,194 Final Office Action dated Dec. 16, 2016.
U.S. Appl. No. 14/977,194 Final Office Action dated Jul. 12, 2018.
U.S. Appl. No. 14/977,194 Final Office Action dated May 21, 2020.
U.S. Appl. No. 14/977,194 Non-Final Office Action dated Aug. 30, 2017.
U.S. Appl. No. 14/977,194 Non-Final Office Action dated Feb. 25, 2016.
U.S. Appl. No. 14/977,194 Non-Final Office Action dated Sep. 26, 2019.
U.S. Appl. No. 16/926,510 Final Office Action mailed Jan. 19, 2023.
U.S. Appl. No. 16/926,510 Non-Final Office Action dated Jul. 8, 2022.
U.S. Appl. No. 16/953,256 Non-Final Office Action dated Jan. 5, 2023.
U.S. Appl. No. 17/946,975 Non-Final Office Action restarting Office Action dated Nov. 17, 2022, mailed on Jan. 11, 2023.
U.S. Appl. No. 17/946,975 Non-Final Office Acton dated Nov. 17, 2022.
U.S. Appl. No. 17/968,413 Non-Final Office Action dated Jan. 3, 2023.
U.S. Food & Drug Administration: Real-World Evidence, pp. 1-3 [Retrieved online Nov. 4, 2020] URL: https://www.fda.goviscience-research/science-and-research-special-topics/real-world-evidence (published Mar. 23, 2020).
Wang et al.: Unsupervised learning of disease progression models. KDD '14: Proceedings of the 20th ACM SIGKDD international conference on Knowledge discovery and data mining, pp. 85-94 URL:https://doi.org/10.1145/2623330.2623754 (Aug. 2014).
Abeler et al., Sleep characteristics in adults with and without chronic musculoskeletal pain: The role of mental distress and pain catastrophizing. Clin J Pain. 2020; 36(9):707-715.
Altman et al., Sleep Disturbance after Hospitalization and Critical Illness: A Systematic Review. Ann Am Thorac Soc. Sep. 2017;14(9):1457-1468. DOI: 10.1513/AnnalsATS.201702-1485R.
Amin et al., Personalized health monitoring using predictive analytics. 2019 IEEE Fifth International Conference on Big Data Computing Service and Applications (BigDataService), 8 pages (2019).
Appelboom et al., Mobile Phone-Connected Wearable Motion Sensors to Assess Postoperative Mobilization. JMIR mHealth and uHealth. 2015;3(3):e78, pp. 1-12.
Araujo et al., Understanding variation in sets of N-of-1 trials. PloS one. 2016;11(12):e0167167, pp. 1-24.
Arlot et al., A survey of cross-validation procedures for model selection. Statistics surveys. 2010;4:40-79.
Arnold et al., Does physical activity increase after total hip or knee arthroplasty for osteoarthritis? a systematic review. J Orthop Sports Phys Ther. Jun. 2016;46(6):431-442.
Aronow et al., Estimating average causal effects under interference between units. arXiv preprint arXiv:13056156. 2013;3(4):16, pp. 1-40.
Athey et al., Machine learning methods for estimating heterogeneous causal effects.arXiv:150401132v1 [statML] Apr. 5, 2015. 2015:1-24.
Avati et al., Improving palliative care with deep learning. BMC Med Inform Decis Mak. 18(Suppl 4):122, pp. 1-10 (2018).
Backman et al., Case studies, single-subject research, and N of 1 randomized trials: comparisons and contrasts. Am J Phys Med Rehabil. 1999;78(2):170-176.
Balandat et al., New tools for econometric analysis of high-frequency time series data-application to demand-side management in electricity markets. University of California, Berkeley. 2016; 221 pages.
Bang et al., Doubly robust estimation in missing data and causal inference models. Biometrics. 2005;61 (4) :962-973.
Bang et al., Total hip and total knee arthroplasties: trends and disparities revisited. Am J Orthop . Sep. 2010;39(9):E95-102.
Bartlett et al., Organizational research: determining appropriate sample size in survey research. Inf Tech Learn and Perf J. 19(1):43-50 (2001).
Bender et al., On the dangers of stochasticparrots: Can language models be too big? Proceedings of the 2021 ACM Conference onFairness, Accountability, and Transparency. 2021;610-623.

(56) References Cited

OTHER PUBLICATIONS

Bühlmann, Invariance, causality and robustness. Statistical Science. 2020;35(3):404-426.

Bindawas et al., Trajectories in functional recovery for patients receiving inpatient rehabilitation for unilateral hip or knee replacement. Arch Gerontol Geriatr. 2014;58(3):344-349.

Borbély, A two process model of sleep regulation. Hum neurobiol. 1982;1(3):195-204.

Bradshaw et al., Influenza Surveillance Using Wearable Mobile Health Devices. Online Journal of Public Health Informatics. 2019; 11(1):e249, pp. 1-4.

Brown et al., Language models are few-shot learners. Advances in neural information processing systems. 2020; 33:1877-1901.

Burg et al., Does Stress Result in You Exercising Less? Or Does Exercising Result in You Being Less Stressed? Or Is It Both? Testing the Bi-directional Stress-Exercise Association at the Group and Person (N of 1) Level. Annals of Behavioral Medicine. 2017:1-11.

Carney et al., The consensus sleep diary: standardizing prospective sleep self-monitoring. Sleep. 2012;35(2):287-302.

Chen et al., A Scalable Tree Boosting System. Proceedings of the 22nd ACM SIGKDD International Conference on Knowledge Discovery and Data Mining. New York, NY, USA: ACM; 2016; pp. 785-794.

Chen et al., Making sense of mobile health data: an open architecture to improve individual- and population-level health. Journal of Medical Internet Research. 2012;14(4):e112.

Cheung et al., Are Nomothetic or Ideographic Approaches Superior in Predicting Daily Exercise Behaviors? Methods of Information in Medicine. 2017;56(6):452-460.

Chevance, Day-to-day associations between sleep and physical activity: a set of person-specific analyses in adults with overweight and obesity. Journal of Behavioral Medicine. 2022;45(1):14-27.

Chinoy et al., Performance of seven consumer sleep-tracking devices compared with polysomnography. Sleep. 2021;44(5):zsaa291, pp. 1-16.

Cohen et al., A digital health industry cohort across the health continuum. NPJ Digit Med. 2020; 3:68, pp. 1-10.

Coravos et al., Digital Medicine: A primer on measurement. Digit Biomark. 2019; 3(2):31-71.

Dawid et al., Identifying the consequences of dynamic treatment strategies: A decision-theoretic overview. Statistics Surveys. 2010; 4:184-231.

Dawid et al., Identifying the consequences of dynamic treatment strategies. Research Report, University College London. 2005; 38 pages.

Dawid, Influence diagrams for causal modelling and inference. International Statistical Review. 2002;70(2):161-189.

Daza, Causal analysis of self-tracked time series data using a counterfactual framework for N-of-1 trials. Methods Inf Med. 57(1):e10-e21 (2018).

Daza et al., Effects of sleep deprivation on blood glucose, food cravings, and affect in a non-diabetic: An N-of-1 randomized pilot study. Healthcare (Basel). 8(1):6, pp. 1-17 (2019).

Daza, Person as Population: A Longitudinal View of Single-Subject Causal Inference for Analyzing Self-Tracked Health Data. arXiv preprint arXiv:190103423. 2019, 18 pages.

Deering et al., Accelerating Research With Technology: Rapid Recruitment for a Large-Scale Web-Based Sleep Study. JMIR Res Protoc. Jan. 2019;8(1):e10974, pp. 1-11.

Dolata et al., Influence of age on the outcome of rehabilitation after total hip replacement. Pol Orthop Traumatol. 78:109-113 (2013).

Dong et al., Familial natural short sleep mutations reduce Alzheimer pathology in mice. Iscience. 2022;25(4):103964, pp. 1-16.

Duan et al., Single-patient (n-of-1) trials: a pragmatic clinical decision methodology for patient-centered comparative effectiveness research. J Clin Epidemiol. 2013;66(8):S21-S28.

Dyer et al., A critical review of the long-term disability outcomes following hip fracture. BMC Geriatr. Sep. 2016;16:158, pp. 1-18.

Eichler, Causal inference in time series analysis. Causality: Statistical Perspectives and Applications. 2012:327-354.

Ei-Galaly et al., Can Machine-learning Algorithms Predict Early Revision TKA in the Danish Knee Arthroplasty Registry? Clin Orthop Relat Res. 2020; 478:2088-2101.

Enshaeifar et al., Machine learning methods for detecting urinary tract infection and analysing daily living activities in people with dementia. PLoS One. 14(1):e0209909, pp. 1-22 (2019).

Estrin, Small data, where n=me. Communications of the ACM. 2014;57(4):32-34.

Gabler et al., N-of-1 trials in the medical literature: a systematic review. Med Care. 2011;49(8):761-768.

Garfield, Sleep duration: A review of genome-wide association studies (GWAS) in adults from 2007 to 2020. Sleep Medicine Reviews. 2021; 56:101413, pp. 1-9.

Gastaldi, Shake-shake regularization. arXiv preprint arXiv: 1705.07485. 2017; pp. 1-10.

Goldsack et al., Verification, analytical validation, and clinical validation (V3): the foundation of determining fit-for-purpose for Biometric Monitoring Technologies (BioMeTs). NPJ Digit Med. 2020; 3:55, pp. 1-10.

Goldsmith et al., Generalized multilevel function-on-scalar regression and principal component analysis. Biometrics. 2015;71(2):344-353.

Greenland et al., Confounding and collapsibility in causal inference. Statistical science. 1999:29-46.

Greenland et al., Identifiability, exchangeability and confounding revisited. Epidemiologic Perspectives & Innovations. 2009;6(1):4, pp. 1-9.

Guyatt et al., Determining optimal therapy—randomized trials in individual patients. N Engl J Med. 1986;314(14):889-892.

Guyatt et al., The n-of-1 Randomized Controlled Trial: Clinical Usefulness: Our Three-Year Experience. Annals of Internal Medicine. 1990;112(4):293-299.

Haberkamp et al., European regulators' views on a wearable-derived performance measurement of ambulation for Duchenne muscular dystrophy regulatory trials. Neuromuscul Disord. 2019;29(7):514-516.

Haghayegh et al., Accuracy of wristband Fitbit models in assessing sleep: systematic review and meta-analysis. Journal of medical Internet research. 2019;21(11):e16273, pp. 1-17.

Hallgrimsson et al., Learning Individualized Cardiovascular Responses from Large-scale Wearable Sensors Data. arXiv preprint arXiv:1812.01696. 2018; pp. 1-5.

Hansen, The prognostic analogue of the propensity score. Biometrika. 2008;95(2):481-488.

He et al., The transcriptional repressor DEC2 regulates sleep length in mammals. Science. 2009;325(5942):866-870.

Hekler et al., Why we need a small data paradigm. BMC medicine. 2019;17(1):1-9.

Hernan et al., Estimating causal effects from epidemiological data. Journal of Epidemiology and Community Health. 2006;60(7):578-586.

Hirano et al., Estimation of causal effects using propensity score weighting: An application to data on right heart catheterization. Health Services and Outcomes research methodology. 2001;2(3):259-278.

Holland et al., Statistics and causal inference. Journal of the American Statistical Association. 1986;81 (396) :945-960.

Horne et al., A self-assessment questionnaire to determine morningness-eveningness in human circadian rhythms. International journal of chronobiology. 1976; author manuscript, 13 pages.

Horvitz et al., A generalization of sampling without replacement from a finite universe. Journal of the American Statistical Association. 1952;47(260):663-685.

Hudgens et al., Toward causal inference with interference. J Am Stat Assoc. 2008;103(482):832-842.

Jonker et al., Postoperative recovery of accelerometer-based physical activity in older cancer patients. Eur J Surg Oncol. 2020; 46:2083-2090. DOI: 10.1016/j.ejso.2020.06.012.

Kalmbach et al., Genetic basis of chronotype in humans: insights from three landmark GWAS. Sleep. 2017;40(2), pp. 1-10.

(56) References Cited

OTHER PUBLICATIONS

Khosla et al., Consumer sleep technol-ogy: an American Academy of Sleep Medicine position statement. Journal of clinical sleep medicine. 2018;14(5):877-880.

Kingma et al., Adam: A method for stochastic optimization. arXiv preprintarXiv: 1412.6980. 2014; pp. 1-15.

Kolbeinsson et al., Self-supervision of wearable sensors time-series data for influenza detection. arXiv preprint arXiv:2112.13755. 2021; pp. 1-5.

Kravitz et al., Design and Implementation of N-of-1 Trials: A User's Guide. AHRQ Publication No. 13(14)-EHC122-EF. Rockville, MD: Agency for Healthcare Research and Quality; Feb. 2014; 94pages.

Kumar et al., Design, Recruitment, and Baseline Characteristics of a Virtual 1-Year Mental Health Study on Behavioral Data and Health Outcomes: Observational Study. JMIR Mental Health. 2020;7(7):e17075, pp. 10-12.

Kuroda et al., Patient-related risk factors associated with less favourable outcomes following hip arthroscopy. Bone Joint J. 2020; 102-B(7):822-831.

Labrique et al., Best practices in scaling digital health in low and middle income countries. Global Health. 2018;14(1):103, pp. 1-8.

Li et al., Digital health: Tracking physiomes and activity using wearable biosensors reveals useful health-related information. PLoS Biology. 2017; 15(1): e2001402, pp. 1-30.

Liang et al., Accuracy of Fitbit Wristbands in Measuring Sleep Stage Transitions and the Effect of User-Specific Factors. JMIR Mhealth Uhealth. Jun. 2019;7(6):e13384, pp. 1-13.

Lillie et al., The n-of-1 clinical trial: the ultimate strategy for individualizing medicine? Per Med. 2011;8(2):161-173.

Lin et al., Surgical Strategy for the Chronic Achilles Tendon Rupture. Biomed Res Int. 2016; 2016:1416971, pp. 1-8.

Lunceford et al., Stratification and weighting via the propensity score in estimation of causal treatment effects: A comparative study. Statistics in Medicine. 2004;23(19):2937-2960.

Lzmailova et al., Remote digital monitoring for medical product development. Clin Transl Sci. 2020; 14(1): 94-101.

Magaziner et al., Recovery after hip fracture: interventions and their timing to address deficits and desired outcomes—evidence from The Baltimore Hip Studies. Nestle Nutr Inst Workshop Ser. 2015;83:71-81.

Mahendraratnam et al., Determining Real-World Data's Fitness for Use and the Role of Reliability. Duke Margolis center for health policy, 54 pages (2019) Available at: https://healthpolicy.duke.edu/sites/default/files/2019-11/rwd_reliability.pdf.

Malenica et al., Adaptive Sequential Design for a Single Time-Series. arXiv preprint arXiv:210200102. 2021; pp. 1-64.

Mallinson et al., Subjective sleep measurement: comparing sleep diary to questionnaire. Nature and Science of Sleep. 2019;11:197.

Marinsek et al., Measuring COVID-19 and influenza in the real world via person-generated health data. bioRxiv medRxiv preprint. 23pages (2020).

Matthews, Multi-period crossover trials. Stat Methods Med Res. 1994; 3(4):383-405.

Merrill et al., Self-supervised pretraining and transfer learning enable flu andcovid-19 predictions in small mobile sensing datasets. arXiv preprint arXiv:2205.13607. 2022; 11 pages.

Mezlini et al., Precision recruitment for high-risk participants in a COVID-19 cohort study Contemp Clin Trials Commun. 2023; 33:101113, pp. 1-4.

Mitchell et al., Model cards for model reporting. arXiv:1810.03993. 2019; pp. 1-10.

Montes et al., Step count reliability and validity of five wear-able technology devices while walking and jogging in both a free motion setting and on a treadmill. International Journal of Exercise Science. 2020;13(7):410.

Moraffah et al., Causal inference for time series analysis: Problems, methods and evaluation. Knowledge and Information Systems. 2021:1-45.

Mueller et al., Continuous monitoring of patient mobility for 18 months using inertial sensors following traumatic knee injury: A Case Study. Digit Biomark. 2018; 2(2):79-89.

Naughton, A starter kit for undertaking n-of-1 trials. European Health Psychologist. 2014;16(5):196-205.

Neto et al., On the analysis of personalized medication response and classification of case vs control patients in mobile health studies: the mPower case study. arXiv preprint arXiv:170609574. 2017; 27 pages.

Neto et al., Towards personalized causal inference of medication response in mobile health: an instrumental variable approach for randomized trials with imperfect compliance. arXiv preprint arXiv:160401055. 2016, 38 pages.

Neyman, On the application of probability theory to agricultural experiments. Essay on principles. Section 9. Statistical Science. 1923, tr 1990;5(4):465-480. Translated and edited by D.M. Dabrowska and T.P. Speed from the Polish original, which appeared in Roczniki Nauk Rolniczych Tom X (1923) 1-51 (Annals of Agricultural Sciences).

O'Driscoll et al., How well do activity monitors estimate energy expenditure? A systematic review and meta-analysis of the validity of current technologies. Br J Sports Med. Mar. 2020;54(6):332-340.

OECD. Health at a Glance 2019: OECD Indicators. Health at a Glance 2019. 2019; 243 pages. DOI: 10.1787/19991312.

Orloff et al. The future of drug development: Advancing clinicaltrial design. Nature reviews Drug discovery, 2009; 8(12):949-957.

Passias et al., Total Knee Arthroplasty in Patients of Advanced Age: A Look at Outcomes and Complications. J Knee Surg. Jan. 2020;33(1):1-7.

Pearl, Causal diagrams for empirical research. Biometrika. 1995;82(4):669-688.

Pearl et al., Probabilistic evaluation of sequential plans from causal models with hidden variables. In: Proceedings of the Eleventh Conference on Uncertainty in Artificial Intelligence. Morgan Kaufmann Publishers Inc.; 1995. p. 444-453.

Piau et al., Current state of digital biomarker technologies for real-life, home-based monitoring of cognitive function for mild cognitive impairment to mild alzheimer disease and implications for clinical care: systematic review. J Med Internet Res. 2019;21(8):e12785, pp. 1-13.

Ponterotto, Qualitative research in counseling psychology: A primer on research paradigms and philosophy of science. Journal of Counseling Psychology. 2005;52(2):126-136.

Radin et al., Harnessing wearable device data to improve state-level real-time surveillance of influenz, a-like illness in the USA: a population-based study. The Lancet Digital Health. 2020;2(2):E85-E93.

Rae et al. Scaling language models: Methods, analysis & insightsfrom training gopher. arXiv preprint arXiv:2112.11446. 2021; pp. 1-120.

Ramesh et al., Hierarchical text-conditionalimage generation with clip latents. arXiv preprint arXiv:2204.06125. 2022; 27 pages.

Ramirez et al.: Continuous Digital Assessment for Weight Loss Surgery Patients. Digit Biomark. 4(1):13-20 doi:10.1159/000506417 (2020).

Reed et al., A generalist agent. arXiv preprintarXiv:2205.06175. 2022; pp. 1-42.

Robins, A new approach to causal inference in mortality studies with a sustained exposure period application to control of the healthy worker survivor effect. Mathematical Modelling. 1986;7(9-12):1393-1512.

Robins et al., Marginal structural models and causal inference in epidemiology. Epidemiology. 2000;11:550-560.

Robins et al., Estimation of the causal effects of time-varying exposures. Longitudinal Data Analysis. 2009; Ch. 23, 553-599.

Robins, Marginal structural models. 1997 Proceedings of the section on Bayesian statistical science. 1997:1-10.

Roenneberg et al., Life between clocks: daily temporal patterns of human chronotypes. Journal of biological rhythms. 2003;18(1):80-90.

Rombach, High-resolution image syn-thesis with latent diffusion models. Proceedings of the IEEE/CVF Conference on ComputerVision and Pattern Recognition. 2022; 10684-10695.

(56) References Cited

OTHER PUBLICATIONS

Rosenbaum et al., The central role of the propensity score in observational studies for causal effects. Biometrika. 1983;70(1):41-55.

Rubin, Comment: Neyman (1923) and causal inference in experiments and observational studies. Statistical Science. 1990;5(4):472-480.

Rubin, Estimating causal effects of treatments in randomized and nonrandomized studies. Journal of Educational Psychology. 1974;66(5):688-701.

Rubin, Randomization analysis of experimental data: The Fisher randomization test comment. Journal of the American statistical association. 1980;75(371):591-593.

Salinas et al., DeepAR: Probabilistic forecasting with autoregressive recurrent networks. International Journal of Forecasting. 2019; 36(2020):1181-1191.

Santa Mina et al., Effect of total-body prehabilitation on postoperative outcomes: a systematic review and meta-analysis. Physiotherapy. Sep. 2014;100(3):196-207.

Savje, Average treatment effects in the presence of unknown interference. The Annals of Statistics. 2021;49(2):673-701.

Schmid, Marginal and dynamic regression models for longitudinal data. Statistics in Medicine. 2001;20(21):3295-3311.

Schork, Personalized medicine: Time for one-person trials. Nature. 2015;520(7549):609-611.

Senn, Mastering variation: variance components and personalised medicine 2016;35(7):966- 977.

Shamseer et al., Consort extension for reporting N-of-1 trials (CENT) 2015: Explanation and elaboration. Journal of Clinical Epidemiology. 2016;76:18-46.

Shapiro et al., Characterizing COVID-19 and influenza illnesses in the real world via person-generated health data. Patterns (NY). 2020; 2(1):100188, pp. 1-14.

Shi et al., A rare mutation of /31-adrenergic receptor affects sleep/wake behaviors. Neuron. 2019;103(6):1044-1055.

Soleimani et al., Treatment-response models for counterfactual reasoning with continuous-time, continuous-valued interventions. arXiv preprint arXiv:1704.02038. 2017; pp. 1-11.

Stevens-Lapsley et al., Comparison of self-reported knee injury and osteoarthritis outcome score to performance measures in patients after total knee arthroplasty. PM R. 2011; 3(6):541-549; quiz 549.

Su et al., Improve postoperative sleep: what can we do? Curr Opin Anaesthesiol. Feb. 2018;31(1):83-8.

Tomakv et al., A clinically applicable approach to continuous prediction of future acute kidney injury. Nature. 2019; 572(7767):116-119.

Unknown, Estimated Influenza Illnesses, Medical visits, Hospitalizations, and Deaths in the United States—2018-2019 influenza season. CDC. 2020; 5 pages. Available at https://web.archive.org/web/20200128214342/https://www.cdc.gov/flu/about/burden/2018-2019.html.

U.S. Appl. No. 18/156,010 Final Office Action dated Sep. 11, 2023.

Van Calster et al., Topic Group "Evaluating diagnostic tests and prediction models" of the Stratos initiative. Calibration: the Achilles heel of predictive analytics. BMC Med. Dec. 2019;17(1):230, pp. 1-7.

Van Den Oord et al., Pixel recurrent neural networks. 33rd International Conference on Machine Learning. 2016; 1747-1756, 10 pages.

Van Den Oord et al., Wavenet: A generative model for raw audio. arXiv preprint arXiv: 1609.03499. 2016, pp. 1-15.

Vanderweele et al., Directed acyclic graphs, sufficient causes, and the properties of conditioning on a common effect. Am J Epidemiol. 2007; 166(9):1096-1104.

Vaswani et al., Attention is all you need. NeurIPS Proceedings. Advances in Neural Information Processing Systems 30 (NIPS 2017). 2017; 11 pages. Available at https://papers.nips.cc/paper_files/paper/2017/hash/3f5ee243547dee91fbd053c1c4a845aa-Abstract.html.

Viboud et al., Fitbit-informed influenza forecasts. Lancet Digit Health. 2020; 2(2):e54-e55.

Vieira et al., Dynamic modelling of n-of-1 data: powerful and flexible data analytics applied to individualised studies. Health Psychology Review. 2017;11(3):222-234.

Vohra et al., Consort extension for reporting N-of-1 trials (CENT) 2015 Statement. Journal of Clinical Epidemiology. 2016;76:9-17.

Wang Y., Causal Inference under Temporal and Spatial Interference. arXiv preprint arXiv:210615074. 2021; 57 pages.

Yang Y., Consistency of cross validation for comparing regression procedures. The Annals of Statistics. 2007;35(6):2450-2473.

Zeileis et al., An R Package for Testing for Structural Change in Linear Regression Models. J Stat Softw. 2002;7(2), pp. 1-38. DOI: 10.18637/jss.v007.i02.

Zucker et al., Combining single patient (N-of-1) trials to estimate population treatment effects and to evaluate individual patient responses to treatment. J Clin Epidemiol. 1997;50(4):401-410.

Zucker, Individual (N-of-1) trials can be combined to give population comparative treatment effect estimates: methodologic considerations. J Clin Epidemiol. 2010;63(12):1312-1323.

Shillan et al., Use of Machine Learning to Analyse Routinely Collected Intensive Care Unit Data: A Systematic Review. Crit Care. 23(1):284, pp. 1-11 (2019).

\* cited by examiner

500

```
┌─────────────────────────────────────────────────────────┐
│ Gather set of data records corresponding to physical     │
│ statistic data of pool of users, where data records for  │
│ at least a portion of the users contains missingness    │
│                         510                              │
└─────────────────────────────────────────────────────────┘
                           ↓
┌─────────────────────────────────────────────────────────┐
│ Apply missingness of data records to other data records  │
│ in set to generate training dataset                      │
│                         520                              │
└─────────────────────────────────────────────────────────┘
                           ↓
┌─────────────────────────────────────────────────────────┐
│ Train missingness ML model to impute training dataset    │
│ to generate learned representations of the training      │
│ dataset                                                  │
│                         530                              │
└─────────────────────────────────────────────────────────┘
```

FIG. 5

SYSTEMS AND METHODS FOR SELF-SUPERVISED LEARNING BASED ON NATURALLY-OCCURRING PATTERNS OF MISSING DATA

CROSS-REFERENCE

This application claims the benefit of U.S. Provisional Application No. 63/412,054, filed Sep. 30, 2022, U.S. Provisional Application No. 63/306,447, filed Feb. 3, 2022, each of which is entirely incorporated herein by reference.

BACKGROUND

Wearable devices may include sensors which periodically or continuously collect data from a user. This data may include physiological or behavioral information that a wearable device may use to make inferences about the user's health. A machine learning (ML) system may use time-series sensor data to analyze user behavior, detect abnormal health events (such as onset of acute health conditions (AHC) or acute illnesses), and/or monitor chronic health conditions. Wearable devices may improve health data collection by being usable outside of clinic, laboratory, or hospital settings. But wearable device data may contain gaps (e.g., due to a user removing or deactivating a wearable device). These gaps in the data may complicate machine learning analysis of the sensor data.

SUMMARY

Machine learning analysis of sensor data may be substantially complicated by gaps created when wearable devices are deactivated or removed. Machine learning algorithms for computer vision and other fields may be improved by using representations computed from models trained for imputation of masked data, or data that has been partially obscured or deleted. These systems are often referred to as "self-supervised learning" systems. Often, masking is performed by obscuring or removing random portions of data sets used for training. This form of masking may be less effective than a type of masking that matches patterns of "missingness" that naturally occur during wearable device use.

In an aspect, a method is disclosed. The method comprises accessing, by a machine learning system, a set of data records for a plurality of users of a population, the data records representative of physical statistics measured for each of the plurality of users over a time period. At least a subset of the data records comprises patterns of missing data for at least a portion of the time period. The method also comprises generating a set of masked data records by masking at least a subset of the data records in accordance with a pattern of natural missingness from a data record of the set of data records. The method also comprises generating, by the machine learning system, a set of learned representations from at least the set of masked data records; and fine tuning, by the machine learning system, a machine learning model using the set of learned representations, the machine learning model configured to perform a downstream machine learning task. In some embodiments, a data record of the subset of the data records contains missing data different from the pattern of natural missingness. In some embodiments, generating the set of masked data records comprises determining a level of similarity between a data record of the set of data records and a data record of the subset of data records. In some embodiments, generating the set of masked data records comprises dividing the subset of data records into a plurality of groups, using one or more segmentation or clustering techniques, where natural missingness of each data record is only used to mask other data records within a common segment or cluster when generating the training dataset. In some embodiments, the physical statistics comprise physiological data. The physiological data comprise one or more of: resting heart rate, current heart rate, heart rate variability, respiration rate, galvanic skin response, skin temperature, and blood oxygen level. In some embodiments, the physical statistics comprise behavioral data. The behavioral data comprise one or more of: daily number of steps, distance walked, time active, exercise amount, exercise type, time slept, number of times sleep was interrupted, sleep start times, sleep end times, napping, or resting. In some embodiments, the data records comprise time series data. In some embodiments, the data records are generated by personal health sensor devices. In some embodiments, the personal health sensor devices are wearable devices. In some embodiments, the method further comprises using a learned representation of the set of learned representations to identify a subset of data records using one or more clustering or segmentation techniques to perform event detection, to detect or predict onset of an acute health condition, to monitor a chronic health condition, to detect trends, to detect outliers, or to identify users that closely resemble one another in terms of health, behavior, or activity. In an aspect, a system is comprising a computing device comprising at least one processor and instructions executable by the at least one processor to cause the at least one processor to perform operations. The operations comprise accessing, by a machine learning system, a set of data records for a plurality of users of a population, the data records representative of physical statistics measured for each of the plurality of users over a time period. At least a subset of the data records comprises patterns of missing data for at least a portion of the time period. For each data record of the subset of data records, the operations comprise the following. The operations comprise identifying, by the machine learning system, a portion of the time period associated with a pattern of missing data. The operations also comprise generating, by the machine learning system, a masked data record by masking a portion of an additional data record of the set of data records corresponding to the identified portion of the time period. The masking of the additional data record causes the additional data record to resemble a data record comprising a pattern of missing data. The operations comprise generating, by the machine learning system, a training dataset comprising at least the additional data records and corresponding generated masked data records. The operations comprise training, by the machine learning system, a machine learning model using the generated training dataset, the machine learning model configured to predict, for a received data record containing masked data, imputed data corresponding to data obscured by the masking of the received data record. The operations comprise generating, by the machine learning model, a plurality of learned representations. The learned representations are associated with the prediction of the imputed data. The operations comprise fine-tuning, by the machine learning system, a learned representation of the plurality of learned representations to a downstream machine learning task. The downstream machine learning task comprises processing a set of data records that is not from the training dataset. In some embodiments, the additional data record contains missing data different from the identified missing data of the corresponding data record. In some embodiments, the instructions are executable by the at least one processor to cause the at least one processor to perform operations further comprising: determining a level of similarity between a current data record and the additional data record. In some embodiments, the instructions are executable by the at least one processor to cause the at least one processor to perform operations further comprising: dividing the set of data records into a plurality of groups, using one or more segmentation or clustering techniques, where missingness of each data record is only used to mask other data records within the same segment or cluster when generating the training dataset. In some embodiments, the missing data is a result of natural missingness, arising from user behavioral patterns. In some embodiments, the physical statistics comprise physiological data. The physiological data comprise one or more of: resting heart rate, current heart rate, heart rate variability, respiration rate, galvanic skin response, skin temperature, and blood oxygen level. In some embodiments, the physical statistics comprise behavioral data. The behavioral data comprise one or more of daily number of steps, distance walked, time active, exercise amount, exercise type, time slept, number of times sleep was interrupted, sleep start times, sleep end times, napping, or resting. In some embodiments, the data records comprise time series data. In some embodiments, the data records are generated by personal health sensor devices. In some embodiments, the personal health sensor devices are wearable devices. In some embodiments, the instructions are executable by the at least one processor to cause the at least one processor to perform operations further comprising: generating multiple training datasets over a plurality of iterations. In an aspect, a non-transitory computer-readable storage media encoded with instructions executable by one or more processors to cause the at least one processor to perform operations is disclosed. The non-transitory computer-readable storage media performs operations comprising accessing, by a machine learning system, a set of data records for a plurality of users of a population, the data records representative of physical statistics measured for each of the plurality of users over a time period. At least a subset of the data records comprise patterns of missing data for at least a portion of the time period. For each data record of the subset of data records, the operations comprise performing (1) identifying, by the machine learning system, a portion of the time period corresponding to naturally occurring missing data, and (2) generating, by the machine learning system, a masked data record by masking a portion of an additional data record of the set of data records corresponding to the identified portion of the time period, to resemble naturally-occurring patterns of missing data. The operations also comprise generating, by the machine learning system, a training dataset comprising at least the additional data records and the corresponding generated masked data records. The operations also comprise training, by the machine learning system, a machine learning model using the generated training dataset, the machine learning model configured to predict, for a received data record containing masked data, imputed data corresponding to data obscured by the masking of the portion of the data record. The operations also comprise generating, by the machine learning system, a plurality of learned representations as a result of the imputation of the masked data in naturally-occurring patterns of missing data. The operations also comprise fine-tuning, by the machine learning machine learning system, a learned representation of the plurality of learned representations to a downstream task on a set of data records not from the training dataset. In some embodiments, the additional data record contains missing data different from the identified missing data of the corresponding data record. In some embodiments, the instructions are executable by the one or more processors to cause the one or more processors to perform operations further comprising: determining a level of similarity between a current data record and the additional data record. In some embodiments, the instructions are executable by the one or more processors to cause the one or more processors to perform operations further comprising: dividing the set of data records into a plurality of groups, using one or more segmentation or clustering techniques, where missingness of each data record is only used to mask other data records within the same segment or cluster when generating the training dataset. In some embodiments, the missing data is a result of natural missingness, arising from user behavioral patterns. In some embodiments, the physical statistics comprise physiological data. In some embodiments, the physiological data comprise one or more of: resting heart rate, current heart rate, heart rate variability, respiration rate, galvanic skin response, skin temperature, and blood oxygen level. In some embodiments, the physical statistics comprise behavioral data. In some embodiments, the behavioral data comprise one or more of: daily number of steps, distance walked, time active, exercise amount, and exercise type. In some embodiments, the behavioral data comprise one or more of: time slept, number of times sleep was interrupted, sleep start times, sleep end times, napping, resting. In some embodiments, the data records comprise time series data. In some embodiments, the data records are generated by personal health sensor devices. In some embodiments, the personal health sensor devices are wearable devices. In some embodiments, the instructions are executable by the one or more processors to cause the one or more processors to perform operations further comprising: generating multiple training datasets over a plurality of iterations. In some embodiments, the instructions are executable by the one or more processors to cause the one or more processors to perform operations further comprising: identifying a subset of data records using one or more clustering or segmentation techniques to perform event detection. In some embodiments, the instructions are executable by the one or more processors to cause the one or more processors to perform operations further comprising: using the learned representation to detect or predict onset of an acute health condition. In some embodiments, the instructions are executable by the one or more processors to cause the one or more processors to perform operations further comprising: using the learned representation to monitor a chronic health condition. In some embodiments, the instructions are executable by the one or more processors to cause the one or more processors to perform operations further comprising: using the learned representation detect trends. In some embodiments, the instructions are executable by the one or more processors to cause the one or more processors to perform operations further comprising: using the learned representation detect outliers. In an aspect, a system comprising a computing device comprising at least one processor and instructions executable by the at least one processor to provide a machine learning application is disclosed. The system comprises a physical statistic data module configured to access a set of data records for a plurality of users of a population, the data records representative of physical statistics measured for each of the plurality of users over a time period. At least a subset of the data records contain naturally occurring missing data for at least a portion of the time period. The system also comprises a missingness dataset processing module configured to, for each data record of the subset of data records: (1) identify a portion of the time period corresponding to naturally occurring missing data, (2) generate a masked data record by masking a portion of an additional data record of the set of data records corresponding to the identified portion of the time period, and (3) generate a training dataset comprising at least the additional data records and the corresponding generated masked data records. The system also comprises a missingness machine learning training module configured to train a self-supervised machine learning model using the generated training dataset, the machine learning model configured to predict, for a received data record containing masked data, imputed data corresponding to the original un-masked data of the received data record. The system also comprises a fine-tuned ML module configured to: (1) receive a set of input data records, where each data record of the set of input data records contain missing data, (2) use the learned representations from the trained machine learning model to fine-tune (continue training) the self-supervised model to the input data records, whether to predict labels in classification or regression tasks (in the case of labeled data, e.g., detect onset of flu) or to aggregate, complete, extend the dataset, in the case of unlabeled data (e.g., imputing missing data), and (3) a learned representation analysis module configured to use the learned representation to perform one or more of: event detection, detect onset of an acute health condition, predict onset of an acute health condition, monitor a chronic health condition, detect trends, and detect outliers. In some embodiments, the missingness ML training module is associated with a missingness ML model store. In some embodiments, the fine-tuning ML module is associated with a fine-tuned ML model store. In some embodiments, the additional data record contains missing data different from the identified missing data of the corresponding data record. In some embodiments, the missingness dataset processing module is further configured to determine a level of similarity between a current data record and the additional data record. In some embodiments, the missingness dataset processing module is further configured to divide the set of data records into a plurality of groups, using one or more segmentation or clustering techniques, where missingness of each data record is only used to mask other data records within the same segment or cluster when generating the training dataset. In some embodiments, the missing data is a result of natural missingness, arising from user behavioral patterns. In some embodiments, the physical statistics comprise physiological data. In some embodiments, the physiological data comprise one or more of: resting heart rate, current heart rate, heart rate variability, respiration rate, galvanic skin response, skin temperature, and blood oxygen level. In some embodiments, the physical statistics comprise behavioral data. In some embodiments, the behavioral data comprise one or more of: daily number of steps, distance walked, time active, exercise amount, and exercise type. In some embodiments, the behavioral data comprise one or more of: time slept, number of times sleep was interrupted, sleep start times, sleep end times, napping, and resting. In some embodiments, the data records comprise time series data. In some embodiments, the data records are generated by personal health sensor devices. In some embodiments, the personal health sensor devices are wearable devices. In some embodiments, the missingness dataset processing module is further configured to generate multiple training datasets over a plurality of iterations. In an aspect, a non-transitory computer-readable storage media is disclosed. The non-transitory computer-readable storage is encoded with instructions executable by one or more processors to create a machine learning system comprising: (1) a physical statistic data module configured to access a set of data records for a plurality of users of a population, the data records representative of physical statistics measured for each of the plurality of users over a time period. At least a subset of the data records contain missing data for at least a portion of the time period; (2) a missingness dataset processing module configured to, for each data record of the subset of data records: (i) identify a portion of the time period corresponding to naturally occurring missing data for some user, (ii) generate a masked data record by masking a portion of another data record (belonging to a different user or at a different time) of the set of data records corresponding to the identified portion of the time period in the first data record, and (iii) generate a training dataset comprising at least the additional data records and the corresponding generated masked data records. The machine learning system also comprises a missingness machine learning (ML) training module configured to: (1) receive a set of input data records (as output by the missingness dataset processing model), where each data record of the set of input data records contain masked data, and their correspondent un-masked ground truth, (2) generate a set of imputed data records corresponding to the set of input data records where the masked data of the input data records is filled in with imputed data predicted by the model, (3) compare the set of imputed data records with their correspondent ground truth to train the self-supervised machine learning model, which as a byproduct is configured to generate a learned representation from received data records. The system also comprises a fine-tuned ML module configured to: (1) receive a set of input data records, where each data record of the set of input data records contain missing data, (2) use the learned representations from the trained machine learning model to fine-tune (continue training) the self-supervised model to the input data records, whether to predict labels in classification or regression tasks (in the case of labeled data, e.g., detect onset of flu) or to aggregate, complete, extend the dataset, in the case of unlabeled data (e.g., imputing missing data). The system also comprises a learned representation analysis module configured to use the learned representation to perform one or more of: event detection, detect onset of an acute health condition, predict onset of an acute health condition, monitor a chronic health condition, detect trends, and detect outliers. In some embodiments, the missingness ML training module is associated with a missingness ML model store. In some embodiments, the fine-tuning ML module is associated with a fine-tuned ML model store. In some embodiments, the additional data record contains missing data different from the identified missing data of the corresponding data record. In some embodiments, the missingness dataset processing module is further configured to determine a level of similarity between a current data record and the additional data record. In some embodiments, the missingness dataset processing module is further configured to divide the set of data records into a plurality of groups, using one or more segmentation or clustering techniques, where missingness of each data record is only used to mask other data records within the same segment or cluster when generating the training dataset. In some embodiments, the missing data is a result of natural missingness, arising from user behavioral patterns. In some embodiments, the physical statistics comprise physiological data. In some embodiments, the physiological data comprise one or more of: resting heart rate, current heart rate, heart rate variability, respiration rate, galvanic skin response, skin temperature, and blood oxygen level. In some embodiments, the physical statistics comprise behavioral data. In some embodiments, the behavioral data comprise one or more of: daily number of steps, distance walked, time active, exercise amount, and exercise type. In some embodiments, the behavioral data comprise one or more of: time slept, number of times sleep was interrupted, sleep start times, sleep end times, napping, resting. In some embodiments, the data records comprise time series data. In some embodiments, the data records are generated by personal health sensor devices. In some embodiments, the personal health sensor devices are wearable devices. In some embodiments, the missingness dataset processing module is further configured to generate multiple training datasets over a plurality of iterations. In an aspect, a computer-implemented method of training a machine learning model to generate inferences from wearable sensor data is disclosed. The method comprises retrieving a first set of wearable sensor data from a plurality of subjects. The method also comprises selectively masking portions of at least a subset of the first set of wearable sensor data. The masked portions are associated with naturally-occurring periods of missing data. The method also comprises creating a training set comprising at least the subset of the wearable sensor data. The method also comprises training the machine learning model to impute data to the masked portions of the subset of wearable sensor data. The machine learning model produces at least one learned representation from the training. The method also comprises fine-tuning the at least one learned representation by using the machine learning model to process a second set of wearable sensor data. In some embodiments, the machine learning task is imputation, regression, segmentation, or classification.

In some embodiments, at least a portion of the wearable sensor data is synthetically generated. Synthetically generated data may closely resemble or approximate data collected from wearable device sensors. Synthetically generating the portion of the wearable sensor data comprises: providing a set of time series wearable sensor data. In some embodiments, synthetic data generation also comprises generating a plurality of embeddings from the time series wearable data. An embedding comprises a sequence of values. A value of the sequence is associated with a position of a set of positions. Synthetic data generation also comprises predicting a value for a position of the set of positions not associated with a value of the sequence by processing the plurality of embeddings with a machine learning model. In some embodiments, the machine learning model comprises an attention mechanism. In some embodiments, the attention mechanism is a multi-head attention mechanism. At least a portion of an attention weight matrix generated from processing the plurality of embeddings is masked. In an aspect, a method for synthetically generating synthetic data is disclosed. The method comprises providing a set of time series wearable sensor data. The method also comprises generating a plurality of embeddings from the time series wearable data. An embedding comprises a sequence of values. A value of the sequence is associated with a position in time of a set of positions in time. The method also comprises predicting a value for a position in time of the set of positions in time not associated with a value of the sequence by processing the plurality of embeddings with a machine learning model. The machine learning model comprises an attention mechanism. At least a portion of an attention weight matrix generated from processing the plurality of embeddings is masked. In some embodiments, the position in time or the set of positions in time corresponds to a future position in time. In some embodiments, the position in time or the set of positions in time corresponds to a masked position in time.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 5 is a flowchart illustrating an example process for performing self-supervised learning using data records having missing data, in accordance with an embodiment;

Figure 1:
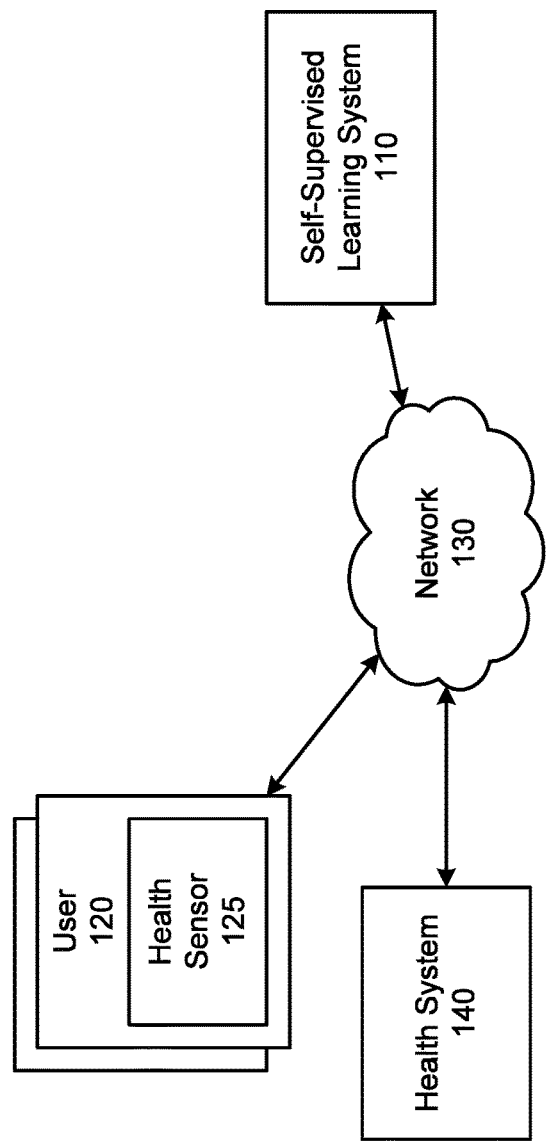
FIG. 1 is a block diagram of a system environment in which a self-supervised learning system operates, in accordance with an embodiment.

The figures depict various embodiments for purposes of illustration only. One skilled in the art will readily recognize from the following discussion that alternative embodiments of the structures and methods illustrated herein may be employed without departing from the principles described herein. The figures use like reference numerals to identify like elements. A letter after a reference numeral, such as "110A," indicates the text refers specifically to the element having that particular reference numeral. A reference numeral in the text without a following letter, such as "102," refers to any or all of the elements in the figures bearing that reference numeral (e.g., "110" in the text refers to reference numerals "110A" and "110B" in the figures).

DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Overview

A self-supervised learning (SSL) system can use unlabeled sensor data collected by wearable devices and reflecting physiological and behavioral data of a user (also referred to as "activity" data or "physical statistics") to identify patterns, trends and/or anomalies in health data for a population or predict health conditions of one or more users. Generally, self-supervised learning systems may analyze unlabeled data, generating learned representations of the data that can in turn be used for various downstream processing tasks (e.g., regression, segmentation, prediction, or classification tasks).

Generating these learned representations using SSL contrasts with feature extraction in supervised learning (SL) systems. SL systems may require smaller, labeled datasets, whereas SSL systems may be able to use large unlabeled datasets. By using smaller, labeled datasets, SL systems may extract features that are closely coupled to the input data, or to downstream processing tasks, which may result in overfitting. But an SSL system may quickly extract useful, complex, and diverse representations that can be reused even as the input data changes, speeding up iteration and development. The SSL system may use the set of learned representations to make a wide variety of health predictions.

Incomplete or missing wearable sensor data may present a problem for an SSL system. Wearable sensor data may be missing when a wearable device is deactivated or not in use, or when a user purposefully redacts or changes data stored on the wearable device. Missing data may cause training problems for the SSL system, potentially compromising the ability of the system to extract useful features, and in turn, complicating downstream processing tasks.

The disclosed self-supervised learning system may mitigate these training problems by masking, or selectively removing or obscuring, portions of data that correspond to commonly-observed or naturally-observed periods of disuse or deactivation of wearable devices. Masking in such a manner, rather than masking random or arbitrary portions of data, may improve the accuracy of the self-supervised learning system after it has been trained, and improve the accuracy of downstream tasks performed (e.g., regression or classification tasks).

In some embodiments, the self-supervised learning system may be trained to impute masked data from sensor data captured by wearables. Learned representations generated in the process of imputing the masked data may be retained and used for other downstream tasks (e.g., regression or segmentation), or even for imputation of wearable device data not seen during training.

Particular Implementations

Disclosed herein is a method for enhancing machine learning analysis of wearable sensor data, by building a machine learning process which makes predictions that consider patterns of naturally-missing data (or "natural missingness"). The method may first comprise accessing, by a machine learning system, a set of data records for a plurality of users who may belong to a population. The data records may comprise time series data. The data records may be generated by personal health sensor devices. The personal health sensor devices may be wearable devices. The data records may be representative of physical statistics measured for each of the plurality of users over a time period. The physical statistics may comprise physiological data. The physiological data may comprise one or more of: resting heart rate, current heart rate, heart rate variability, respiration rate, galvanic skin response, skin temperature, and blood oxygen level. The physical statistics may comprise behavioral data. The behavioral data may comprise one or more of: daily number of steps, distance walked, time active, exercise amount, exercise type, time slept, number of times sleep was interrupted, sleep start times, sleep end times, napping, or resting. At least a subset of the data records may comprise patterns of missing data for at least a portion of the time period. The method may next comprise generating a set of masked data records by masking at least a subset of the data records in accordance with a pattern of natural missingness from a data record of the set of data records. Generating the set of masked data records may comprise determining a level of similarity between a data record of the set of data records and a data record of the subset of data records. Generating the set of masked data records may also comprise dividing the subset of data records into a plurality of groups, using one or more segmentation or clustering techniques, where natural missingness of each data record is only used to mask other data records within a common segment or cluster when generating the training dataset. Then, the method may comprise generating, by the machine learning system, a set of learned representations from at least the set of masked data records. Finally, the method may comprise fine tuning, by the machine learning system, a machine learning model using the set of learned representations. The machine learning model may be configured to perform a downstream machine learning task. The method may comprise using a learned representation of the set of learned representations to identify a subset of data records using one or more clustering or segmentation techniques to perform event detection, to detect or predict an onset of an acute health condition, to monitor a chronic health condition, to detect trends, to detect outliers, or to identify users that closely resemble one another in terms of health, behavior, or activity. Disclosed is a system. The system may comprise a computing device, which may comprise at least one processor and instructions executable by the at least one processor, to cause the at least one processor to perform the following operations. The system may be configured to access, by a machine learning system, a set of data records for a plurality of users of a population. The data records may comprise time series data. At least a subset of the data records may comprise patterns of missing data for at least a portion of the time period. The data records may be representative of physical statistics measured for each of the plurality of users over a time period. The physical statistics may comprise physiological data. The physiological data may comprise one or more of: resting heart rate, current heart rate, heart rate variability, respiration rate, galvanic skin response, skin temperature, and blood oxygen level. The data records may be generated by personal health sensor devices. The personal health sensor devices may be wearable devices. The physical statistics may comprise behavioral data. The behavioral data may comprise one or more of daily number of steps, distance walked, time active, exercise amount, exercise type, time slept, number of times sleep was interrupted, sleep start times, sleep end times, napping, or resting. For each data record of the subset of data records, the system may identify, by the machine learning system, a portion of the time period associated with a pattern of missing data. The system may next generate, by the machine learning system, a masked data record by masking a portion of an additional data record of the set of data records corresponding to the identified portion of the time period. The masking of the additional data record may cause the additional data record to resemble a data record comprising a pattern of missing data. The missing data may be a result of natural missingness, arising from user behavioral patterns. The additional data record may contain missing data different from the identified missing data of the corresponding data record. The system may generate, by the machine learning system, a training dataset comprising at least the additional data records and corresponding generated masked data records. The system may train, by the machine learning system, a machine learning model using the generated training dataset. The machine learning model may be configured to predict, for a received data record containing masked data, imputed data corresponding to data obscured by the masking of the received data record. The system may generate, by the machine learning model, a plurality of learned representations. The learned representations are associated with the prediction of the imputed data. The system may fine-tune, by the machine learning system, a learned representation of the plurality of learned representations to a downstream machine learning task. The downstream machine learning task may comprise processing a set of data records that is not from the training dataset. The instructions may be executable by the at least one processor to cause the at least one processor to perform operations further comprising: determining a level of similarity between a current data record and the additional data record. The instructions may be executable by the at least one processor to cause the at least one processor to perform operations further comprising: dividing the set of data records into a plurality of groups, using one or more segmentation or clustering techniques. Missingness of each data record may be used to mask other data records within the same segment or cluster when generating the training dataset. The instructions may be executable by the at least one processor to cause the at least one processor to perform operations further comprising: generating multiple training datasets over a plurality of iterations. The instructions may be executable by at least the one processor to perform using a learned representation of the set of learned representations to identify a subset of data records using one or more clustering or segmentation techniques to perform event detection, to detect or predict the onset of an acute health condition, to monitor a chronic health condition, to detect trends, to detect outliers, or to identify users that closely resemble one another in terms of health, behavior, or activity. Disclosed is non-transitory computer-readable storage media encoded with instructions executable by one or more processors to cause at least one processor to perform at least the following operations. The first operation may be accessing, by a machine learning system, a set of data records for a plurality of users within a population. The data records may be representative of physical statistics measured for each of the plurality of users over a time period. The physical statistics may comprise physiological data. The physiological data may comprise one or more of: resting heart rate, current heart rate, heart rate variability, respiration rate, galvanic skin response, skin temperature, and blood oxygen level. The data records may be generated by personal health sensor devices. The personal health sensor devices may be wearable devices. The data records may comprise time series data. The physical statistics may comprise behavioral data. The behavioral data may comprise one or more of daily number of steps, distance walked, time active, exercise amount, exercise type, time slept, number of times sleep was interrupted, sleep start times, sleep end times, napping, or resting. At least a subset of the data records may comprise patterns of missing data for at least a portion of the time period. For each data record of the subset of data records, the operations may include identifying, by the machine learning system, a portion of the time period corresponding to naturally occurring missing data, and generating, by the machine learning system, a masked data record by masking a portion of an additional data record of the set of data records corresponding to the identified portion of the time period, to resemble naturally-occurring patterns of missing data. The additional data record may contain missing data different from the identified missing data of the corresponding data record. The missing data may be a result of natural missingness, arising from user behavioral patterns. The operations may also include generating, by the machine learning system, a training dataset comprising at least the additional data records and the corresponding generated masked data records. The operations may also include training, by the machine learning system, a machine learning model using the generated training dataset, the machine learning model configured to predict, for a received data record containing masked data, imputed data corresponding to data obscured by the masking of the portion of the data record. The operations may also include generating, by the machine learning system, a plurality of learned representations as a result of the imputation of the masked data in naturally-occurring patterns of missing data. Finally, the operations may include fine-tuning, by the machine learning machine learning system, a learned representation of the plurality of learned representations to a downstream task on a set of data records not from the training dataset. The instructions may be executable by the at least one processor to cause the at least one processor to perform operations further comprising: determining a level of similarity between a current data record and the additional data record. The instructions may be executable by the at least one processor to cause the at least one processor to perform operations further comprising: dividing the set of data records into a plurality of groups, using one or more segmentation or clustering techniques. Missingness of each data record may be used to mask other data records within the same segment or cluster when generating the training dataset. The instructions may be executable by the at least one processor to cause the at least one processor to perform operations further comprising: generating multiple training datasets over a plurality of iterations. The instructions may be executable by at least the one processor to perform using a learned representation of the set of learned representations to identify a subset of data records using one or more clustering or segmentation techniques to perform event detection, to detect or predict an onset of an acute health condition, to monitor a chronic health condition, to detect trends, to detect outliers, or to identify users that closely resemble one another in terms of health, behavior, or activity. A computer-implemented method of training a machine learning model to generate inferences from wearable sensor data. The method may comprise retrieving a first set of wearable sensor data from a plurality of subjects. The method may next comprise selectively masking portions of at least a subset of the first set of wearable sensor data. The masked portions are associated with naturally-occurring periods of missing data. The method may next comprise creating a training set comprising at least the subset of the wearable sensor data. The method may next comprise training the machine learning model to impute data to the masked portions of the subset of wearable sensor data. The machine learning model may comprise an attention mechanism. The attention mechanism may be a multi-head attention mechanism. The machine learning model produces at least one learned representation from the training. Finally, the method may comprise fine-tuning the at least one learned representation by using the machine learning model to process a second set of wearable sensor data. The method may further comprise performing a machine learning task by processing the at least one learned representation with one or more machine learning algorithms. The machine learning task may be imputation, regression, segmentation, or classification. Disclosed additionally is a method of synthetically generating wearable data. The synthetically wearable data may be used with the natural missingness masking methods disclosed herein. The synthetically generated wearable data may be used for alternative machine learning tasks that do not require natural missingness masking. Synthetically generating a portion of the wearable sensor data may comprise, provided a set of time series wearable data, (1) generating a plurality of embeddings from the time series wearable data. An embedding may comprise a sequence of values. A value of the sequence may be associated with a position of a set of positions. The positions may be associated with different points in time. The method may next comprise (2) predicting a value for a position of the set of positions not associated with a value of the sequence by processing the plurality of embeddings with a machine learning model. The position in time of the set of positions in time may be a future position in time (i.e., temporally ahead of the furthest position associated with a value in the sequence). The position in time of the set of positions in time may correspond to a masked position in time. This may enable the imputation of synthetic data into a missing section of real wearable data. The machine learning model may comprise an attention mechanism. At least a portion of an attention weight matrix generated from processing the plurality of embeddings is masked. A system comprising a computing device comprising at least one processor and instructions executable by the at least one processor to provide a machine learning application is disclosed. The system may comprise (a) a physical statistic data module configured to access a set of data records for a plurality of users of a population, the data records representative of physical statistics measured for each of the plurality of users over a time period, wherein at least a subset of the data records contain naturally occurring missing data for at least a portion of the time period; (b) a missingness dataset processing module configured to, for each data record of the subset of data records: (i) identify a portion of the time period corresponding to naturally occurring missing data, (ii) generate a masked data record by masking a portion of an additional data record of the set of data records corresponding to the identified portion of the time period, and (iii) generate a training dataset comprising at least the additional data records and the corresponding generated masked data records; (c) a missingness machine learning (ML) training module configured to train a self-supervised machine learning model using the generated training dataset, the machine learning model configured to predict, for a received data record containing masked data, imputed data corresponding to the original un-masked data of the received data record; (d) a fine-tuned ML module configured to: (i) receive a set of input data records, where each data record of the set of input data records contain missing data, (ii) use the learned representations from the trained machine learning model to fine-tune (continue training) the self-supervised model to the input data records, whether to predict labels in classification or regression tasks or to aggregate, complete, extend the dataset, in the case of unlabeled data (e.g., imputing missing data) and (iii) a learned representation analysis module configured to use the learned representation to perform one or more of: event detection, detect an onset of an acute health condition, predict an onset of an acute health condition, monitor a chronic health condition, detect trends, and detect outliers. The missingness ML training module may be associated with a missingness ML model store. The fine-tuning ML module may be associated with a fine-tuned ML model store. The additional data record contains missing data different from the identified missing data of the corresponding data record. The missingness dataset processing module may be further configured to determine a level of similarity between a current data record and the additional data record. The missingness dataset processing module may be further configured to divide the set of data records into a plurality of groups, using one or more segmentation or clustering techniques, where missingness of each data record may be only used to mask other data records within the same segment or cluster when generating the training dataset. The missing data may be a result of natural missingness, arising from user behavioral patterns. The physical statistics comprise physiological data. The physiological data comprise one or more of: resting heart rate, current heart rate, heart rate variability, respiration rate, galvanic skin response, skin temperature, and blood oxygen level. The physical statistics may comprise behavioral data. The behavioral data may comprise one or more of: daily number of steps, distance walked, time active, exercise amount, and exercise type. The behavioral data may comprise one or more of: time slept, number of times sleep was interrupted, sleep start times, sleep end times, napping, or resting. The data records may comprise time series data. The data records may be generated by personal health sensor devices. The personal health sensor devices may be wearable devices. The missingness dataset processing module may be further configured to generate multiple training datasets over a plurality of iterations. Disclosed is a non-transitory computer-readable storage media encoded with instructions executable by one or more processors to create a machine learning system. The machine learning system may comprise (a) a physical statistic data module configured to access a set of data records for a plurality of users of a population, the data records representative of physical statistics measured for each of the plurality of users over a time period, with at least a subset of the data records containing missing data for at least a portion of the time period; (b) a missingness dataset processing module configured to, for each data record of the subset of data records: (i) identify a portion of the time period corresponding to naturally occurring missing data for some user, (ii) generate a masked data record by masking a portion of another data record (belonging to a different user or at a different time) of the set of data records corresponding to the identified portion of the time period in the first data record, and (iii) generate a training dataset comprising at least the additional data records and the corresponding generated masked data records; (c) a missingness machine learning (ML) training module configured to: (i) receive a set of input data records (as output by the missingness dataset processing model), where each data record of the set of input data records contain masked data, and their correspondent un-masked ground truth, (ii) generate a set of imputed data records corresponding to the set of input data records where the masked data of the input data records may be filled in with imputed data predicted by the model, (iii) compare the set of imputed data records with their correspondent ground truth to train the self-supervised machine learning model, which as a byproduct may be configured to generate a learned representation from received data records, and (d) a fine-tuned ML module configured to: (i) receive a set of input data records, where each data record of the set of input data records contain missing data, (ii) use the learned representations from the trained machine learning model to fine-tune (continue training) the self-supervised model to the input data records, whether to predict labels in classification or regression tasks (in the case of labeled data, e.g., detect an onset of flu) or to aggregate, complete, extend the dataset, in the case of unlabeled data (e.g., imputing missing data) and; (e) a learned representation analysis module configured to use the learned representation to perform one or more of: event detection, detect an onset of an acute health condition, predict an onset of an acute health condition, monitor a chronic health condition, detect trends, and detect outliers. The missingness ML training module may be associated with a missingness ML model store. The fine-tuning ML module may be associated with a fine-tuned ML model store. The additional data record contains missing data different from the identified missing data of the corresponding data record. The missingness dataset processing module may be further configured to determine a level of similarity between a current data record and the additional data record. The missingness dataset processing module may be further configured to divide the set of data records into a plurality of groups, using one or more segmentation or clustering techniques, where missingness of each data record may be only used to mask other data records within the same segment or cluster when generating the training dataset. The missing data may be a result of natural missingness, arising from user behavioral patterns. The physical statistics may comprise physiological data. The physiological data may comprise one or more of: resting heart rate, current heart rate, heart rate variability, respiration rate, galvanic skin response, skin temperature, and blood oxygen level. The physical statistics may comprise behavioral data. The behavioral data may comprise one or more of: daily number of steps, distance walked, time active, exercise amount, and exercise type. The behavioral data may comprise one or more of: time slept, number of times sleep was interrupted, sleep start times, sleep end times, napping, and resting. The data records may comprise time series data. The data records may be generated by personal health sensor devices. The personal health sensor devices may be wearable devices. The missingness dataset processing module may be further configured to generate multiple training datasets over a plurality of iterations.

System

FIG. 1 is a block diagram of a system environment in which a self-supervised learning system operates, in accordance with an embodiment. The environment 100 of FIG. 1 includes a self-supervised learning system 110, a set of users 120, each associated with one or more health sensors 125, a network 130, and a health system 140.

The self-supervised learning system 110 may comprise a server, server cluster, distributed server, or cloud-based server capable of predicting health condition (e.g., chronic health condition (CHC)) symptoms for a user 120 within a population based on physical statistics received from that user 120. In some embodiments, the self-supervised learning system 110 gathers physical statistics about a set of users 120 within a population (for example, through data from one or more health sensors monitoring the physical statistics of users 120). As used herein, physical statistics are measurements characterizing a user's activity level or current health state (such as from health sensors 125 or other sources). For example, physical statistics can include measurements of the user's vital signs such as body temperature, resting heart rate (RHR), blood pressure, current heart rate (for example, presented as a time series), heart rate variability, respiration rate, or galvanic skin response, measurements of user activity such as daily number of steps, distance walked, time active, or exercise amount, sleep statistics such as time slept, number of times sleep was interrupted, or sleep start and end times, and/or other similar metrics.

The self-supervised learning system 110 can analyze received physical statistic data to extract learned features and/or generate a learned representation of the physical statistic data. In some embodiments, the learned representation may store a transformed, modified, or compressed version of raw physical statistic data. This version of the raw physical statistic data (or wearable device data) may preserve richness of information and useful features that may be used to identify trends and/or outliers among data gathered across a large population, predict health conditions, segment, cluster, or categorize data from different users, and/or the like. The self-supervised learning system 110 will be discussed further below.

Each user 120 of the self-supervised learning system 110 may be a member of a population monitored by the self-supervised learning system 110. In some embodiments, each user 120 is associated with a set of health sensors 125 measuring physical statistics of that user 120. For example, the set of health sensors 125 associated with a user 120 can measure the user's resting heart rate (RHR) over time, a daily number of steps (and/or other measure of activity level such as distance walked), and sleep statistics (such as duration of sleep, number of times sleep was interrupted, sleep start and end times, etc.) for the user 120. Recorded physical statistics from health sensors 125 may be stored as physical statistic data and sent by the health sensor 125 to the self-supervised learning system 110 for analysis. In some implementations, some or all physical statistic data is collected as time series data, or periodically recorded measurements of physical statistics of the user 120 over time. The frequency of measurements included in the physical statistics data sent to the self-supervised learning system 110 can depend on the health sensor 125, user preference selections, and/or the type of physical statistic data being collected. For example, a health sensor 125 may send time series data for average RHR multiple times per day, but only send hours slept data once per day. In some implementations, the health sensor 125 sends physical statistic data to the self-supervised learning system 110 frequently, for example, hourly or in real time.

A health sensor 125 can be a wearable device or other device capable of providing physical statistics about the user 120. For example, a health sensor 125 can be a dedicated fitness tracker, a pedometer, a sleep tracker, a smart watch, smartphone, or mobile device (e.g., a tablet computer or a personal digital assistant (PDA)) with physical statistic monitoring functionality. For example, a health sensor 125 can be a smartphone of the user 120 with an installed physical statistic monitoring application using one or more sensors of the smartphone to measure steps, activity, movement, sleep time, or other physical statistics. An individual user 120 can be associated with multiple health sensors 125 measuring overlapping or distinct physical statistics about the user 120. The physical statistic data gathered by health sensors 125 can be sent to the self-supervised learning system 110 directly from the health sensor 125, manually uploaded to the self-supervised learning system 110 by the associated user 120 or transmitted via a third-party system to the self-supervised learning system 110. For example, the user 120 may authorize a third-party service associated with a health sensor 125 to transmit physical activity data to the self-supervised learning system 110. In some embodiments, a user 120 can interact with health sensors 125 and the self-supervised learning system 110 through a user device such as a mobile device, laptop or desktop computer, or other similar computing device. For example, a user 120 may be able to configure settings of the health sensors 125 through a user device (e.g., turn one or more health sensors 125 on/off, change a sampling rate, etc.). In some embodiments, the user 120 may further be able to provide feedback relating to one or more predictions generated using the self-supervised learning system 110 and/or manually report health information to the self-supervised learning system 110. For example, in some embodiments, the user 120 may, through a user device, report to the self-supervised learning system 110 that they have the flu, which may be used by the self-supervised learning system 110 in training models to recognize features of received physical statistical data indicative of certain health conditions.

A user 120 or a health sensor 125 associated with a user 120 can communicate with the self-supervised learning system 110 over the network 130. The network 130 may be a network or system of networks connecting the self-supervised learning system 110 to the set of users 120 and/or health sensors 125 associated with a user 120. The network 130 may comprise any combination of local area and/or wide area networks, using wired and/or wireless communication systems. In one embodiment, the network 130 uses standard communications technologies and/or protocols. For example, the network 130 can include communication links using technologies such as Ethernet, 3G, 4G, CDMA, WIFI, and Bluetooth. Data exchanged over the network 130 may be represented using any suitable format, such as hypertext markup language (HTML) or extensible markup language (XML). In some embodiments, all or some of the communication links of the network 130 may be encrypted using any suitable technique or techniques. In some implementations, the network 130 also facilitates communication between the self-supervised learning system 110, users 120, and other entities of the environment 100 such as the health system 140.

The health system 140 may be a server, set of servers, server cluster, or other computing system which can create or modify an individual treatment plan and/or perform interventions based on predicted health conditions generated using the self-supervised learning system 110. For example, the health data repository 140 can be a medical provider, doctor, or other entity providing medical care to a user 120 for a health condition. Only one health system 140 is shown in FIG. 1, however, the self-supervised learning system 110 can interface with multiple health systems 140 for different users 120.

Figure 2:
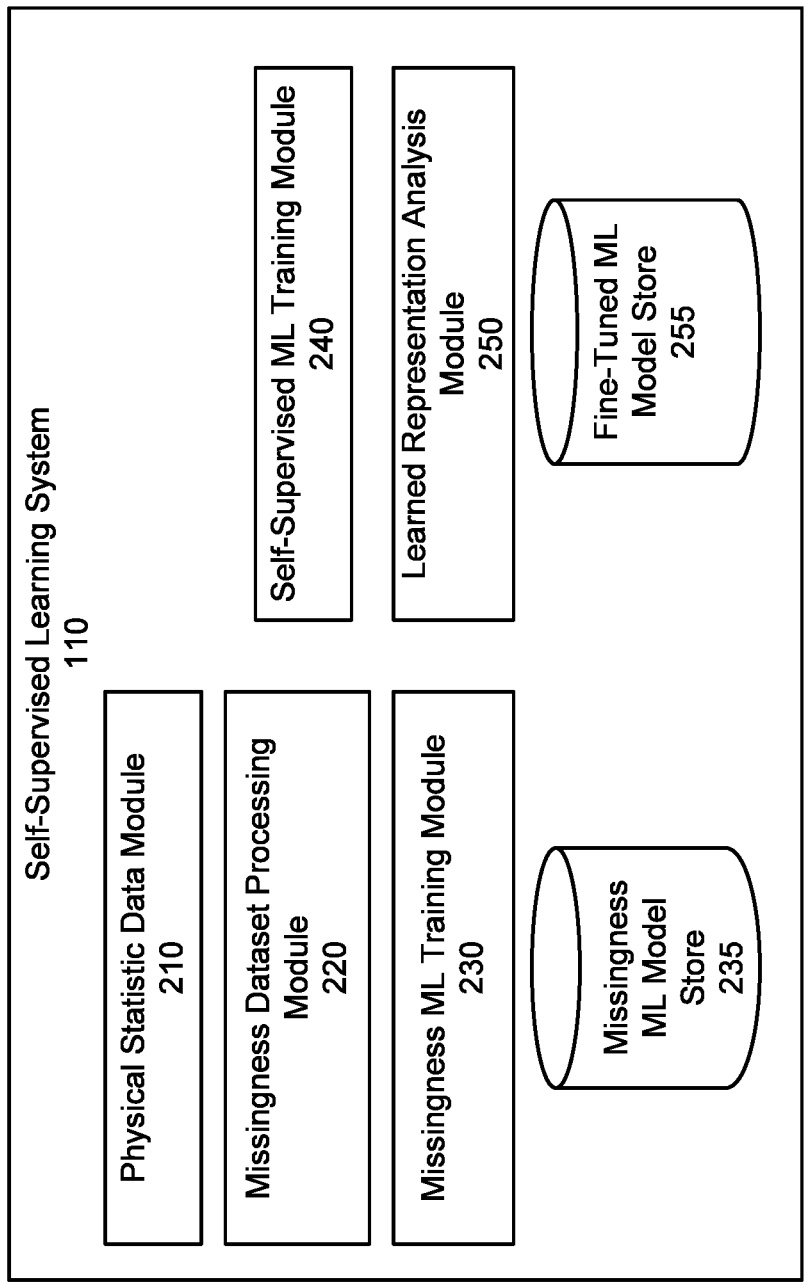
FIG. 2 is a block diagram of a self-supervised learning system, in accordance with an embodiment.

FIG. 2 is a block diagram of a self-supervised learning system, in accordance with an embodiment. FIG. 2 shows the self-supervised learning system 110 including a physical statistic data module 210, a missingness dataset processing module 220, a missingness machine learning (ML) training module 230 with an associated missingness ML model store 235, a learned representation analysis module 240 and a fine-tuning ML module 250 with an associated fine-tuned ML module store 255.

In other embodiments, the self-supervised learning system 110 may include additional, fewer, or different components for various applications. Conventional components such as network interfaces, security functions, load balancers, failover servers, management and network operations consoles, and the like are not shown to not obscure the details of the system architecture.

In some embodiments, self-supervised learning system 110 can monitor a set of users 120 for multiple different physical statistics such as those described above. In some implementations, each module of the self-supervised learning system 110 can simultaneously perform its function for different physical statistics or combinations of physical statistics.

Data Gathering

The physical statistic data module 210 of the self-supervised learning system 110 can monitor a set of physical statistics of the set of users 120. In some implementations, the physical statistic data module 210 gathers time series datasets representing measures of the set of physical statistics of a user over time ("physical statistic data"). The physical statistic data module 210 can receive physical statistic data, process it for use by the self-supervised learning system 110, and store processed and/or unprocessed physical statistic data. As described above, the physical statistic data for a user can include readings from one or more health sensors 125 associated with the user, however the physical statistic data module 210 can collect physical statistic data from other sources, such as by being logged or otherwise manually input by the associated user 120 or by a health care provider of the associated user 120, from a health data repository 140, or from another similar source.

The physical statistic data module 210 can, in some embodiments, preprocess received physical statistic data prior further analysis by the self-supervised learning system 110. The self-supervised learning system 110 can receive physical statistic data from multiple different types or models of health sensors 125 (or other sources) which can report physical statistic data in different formats and using different conventions. For example, the frequency of data points in received time series data can differ between physical statistic data collected from different health sensors 125 (even if both measure the same statistics). In some implementations, the physical statistic data module 210 can standardize received physical statistic data for further analysis, such as by transforming received time series data to be consistent across the set of physical statistic data and/or computing secondary physical statistic data from received physical statistic data. For example, the physical statistic data module 210 can receive physical statistic data for a user 120 including a rolling 5-minute average of heart rate measurements and activity data for a user and preprocess the data to a daily RHR, step count, time spent active, and sleep time (for example, determined based on a combination of time, heart rate, and activity data) for the user 120.

In some embodiments, the physical statistic data module 210 organizes the collected physical statistic data into one or more data records. As used herein, a data record may refer to physical statistic data collected for a particular user over a particular time period (e.g., one day, one week, one month, etc.). A data record may comprise data corresponding to multiple different physical data statistics collected for the user over the time period.

Each physical statistic monitored by the self-supervised learning system 110 can be affected based on the behavior of a user 120 (e.g., whether the user is exercising, is asleep, etc.) and/or a health condition of the user 120 (e.g., whether the user is exhibiting normal health, has the flu, is suffering from allergies, etc.). As such, by analyzing the physical statistics monitored for a given user, predictions can be made relating to user behavior and/or user health condition. For example, in some embodiments, the physical statistic data module 210 can be used for training models to reflect different behaviors and/or health conditions, and to predict behaviors and/or health conditions for an individual user based on received physical statistic data for the user, in real time or near-real time. In some embodiments, the physical statistic data module 210 continuously receives physical statistic data from health sensors 125 or users and preprocesses the physical statistic data for evaluation in real time or near-real time (for example, for predicting the health condition of a user).

Missingness

In some embodiments, the physical statistic data received by the physical statistic data module 210 for a given user may contain missing data (also referred to as "missingness"). For example, where the physical statistic data includes readings from one or more health sensors (e.g., health sensors 125), the physical statistic data may be missing data corresponding to periods of time during which the user has turned off their health sensor, removed their health sensor from their body, neglected to report information to their health sensor, etc. Because this missing data largely arises from user behavioral patterns of device wear-time and usage, the missing data may be referred to as "natural missingness." The presence of missingness may result in the self-supervised learning system 110 having an incomplete picture of the user's physical statistics, which may potentially compromise the ability of the self-supervised learning system 110 to extract features from the user's physical statistic data and/or generate useful inferences pertaining to the user's health from the physical statistic data. For example, in embodiments, where the physical statistic data module 210 organizes the collected physical statistic data into one or more data records, a data record corresponding to physical statistic data for a particular user collected over a particular time period may contain time periods where values for one or more types of physical statistics is missing.

The self-supervised learning system 110 may use learned representations to perform downstream processing tasks (e.g., regression, segmentation, or classification). The effectiveness of the self-supervised learning system 110 in accurately performing these downstream tasks may be highly dependent on the way the input data is masked during the SSL training step.

In some embodiments, techniques based on natural missingness which mask portions of received data records in a manner that more accurately reflects actual patterns of missingness found in received data records are used. For example, natural missingness, instead of being random, may be caused by real-world behaviors exhibited by certain users (e.g., by a user removing their wearable devices containing health sensors 125 when performing certain activities, such as exercising, showering, and/or sleeping, or removing wearable devices for the purpose of battery charging, etc.). By masking input data (e.g., data records for users where such data is available) in a way that reflects patterns of actual missingness, the missingness ML model is trained in a way that can improve the ability of downstream applications to generate predictions and inferences relating to the health and behavior of the users corresponding to the data records. Examples of how masking may be performed based on natural missingness are discussed in greater detail in relation to FIGS. 3 and 4.

Figure 3:
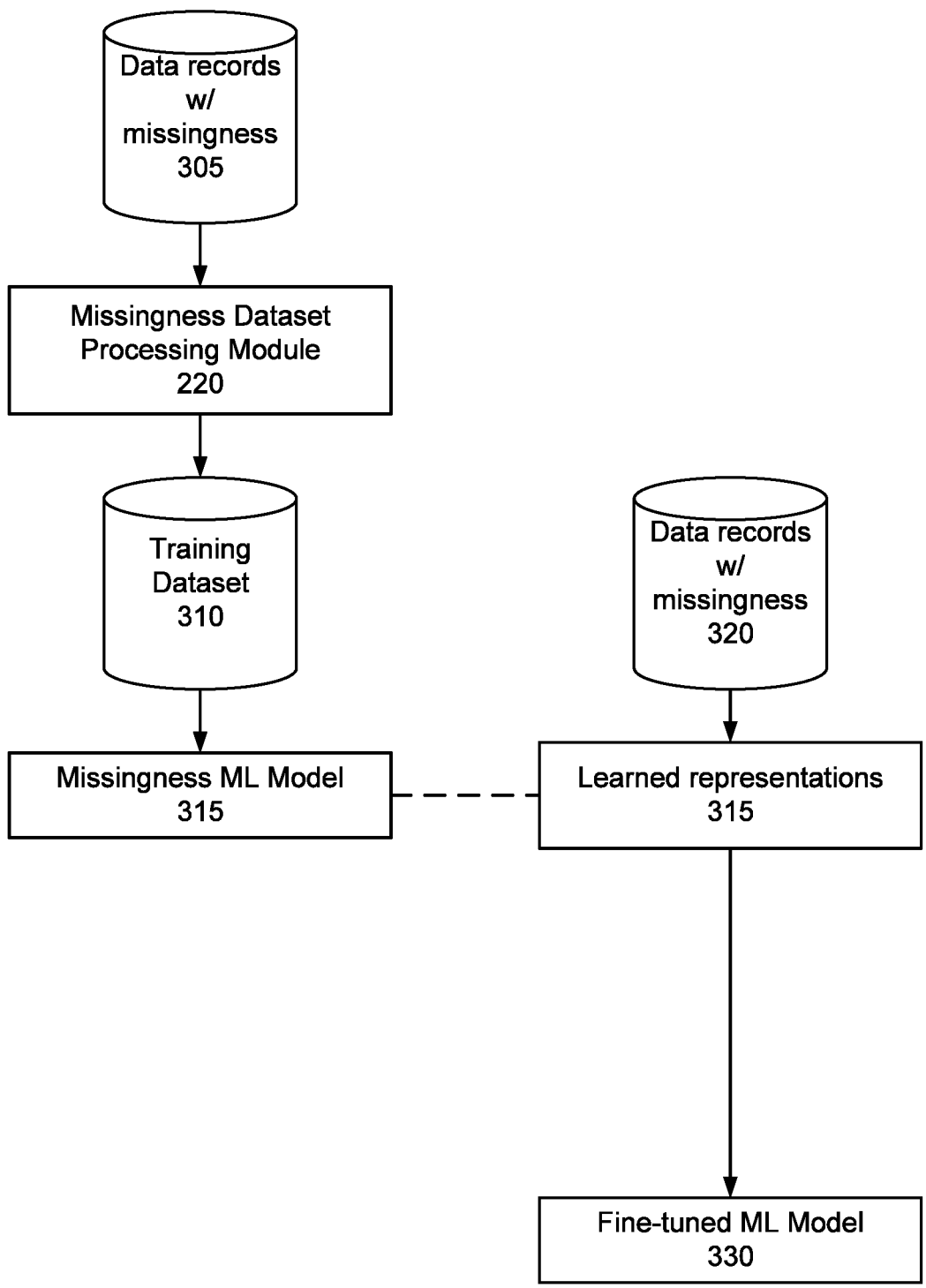
FIG. 3 illustrates a block diagram of operations of the missingness dataset processing module and missingness ML model store, in accordance with an embodiment.

FIG. 3 illustrates a block diagram of operations the missingness dataset processing module 220 and missingness ML model store 235, in accordance with an embodiment. In some embodiments, the missingness dataset processing module 220 receives a set of data records 305 from the physical statistic data module 210 corresponding to physical statistic data collected from a plurality of different users, wherein at least a portion of the records contains missingness. Each data record corresponds to physical statistic data collected from a corresponding user over a particular time period (e.g., one day, one week, one month, etc.). In some embodiments, the data records of the set 305 correspond to data collected over a same time period (e.g., the same day, week, month, etc.). In other embodiments, the data records may correspond to data collected over different time periods.

The missingness dataset processing module 220 processes the dataset 305 to generate a training dataset 310. As discussed above, techniques based on natural missingness which mask portions of received data records in a manner that reflects actual patterns of missingness found in received data records may be used to generate the training dataset 310, to train the missingness ML model to create representations that can serve to more accurately complete downstream ML tasks. In some embodiments, the missingness dataset processing module 220 processes the dataset 305 by masking certain data records of the dataset 305 based upon missingness found in other data records of the dataset 305. By masking based on the actual missingness of received data records, the masked portions of the data records are more likely to reflect natural real-world patterns of missingness. The masked data records are combined with the corresponding original unmasked data records of the dataset 305 to form the training dataset 310. In some embodiments, the missingness dataset processing module 220 generates multiple training datasets 310 over a plurality of iterations, by masking data records of the dataset 305 based upon missingness of other data records of the dataset 305 in different combinations, e.g., to compensate for missingness overlap between different data records, differences in users corresponding to different data records, etc.

Figure 4:
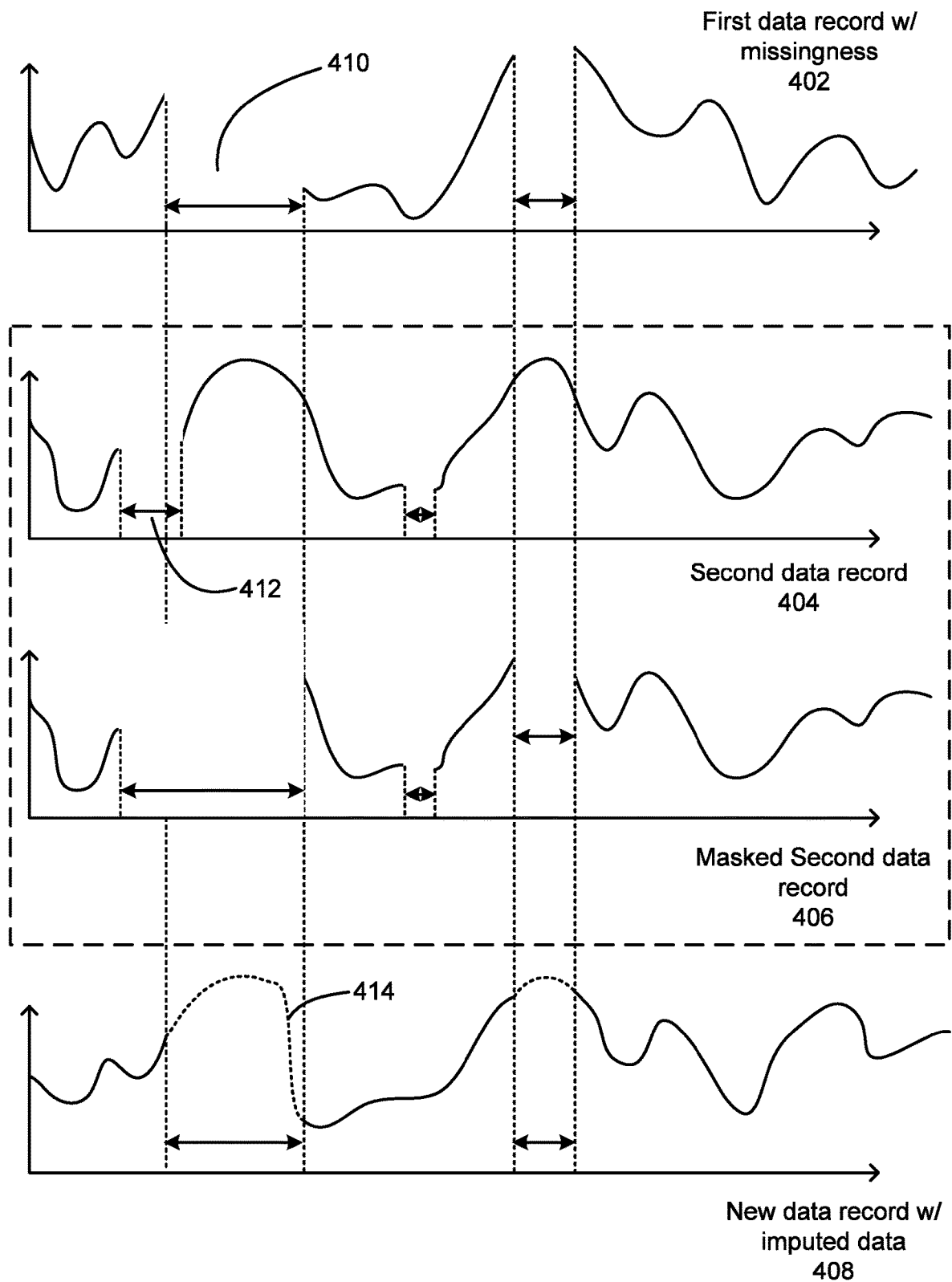
FIG. 4 illustrates an example of generating masked data records from a received dataset, in accordance with an embodiment.

FIG. 4 illustrates an example of generating masked data records from a received dataset, in accordance with an embodiment. For example, FIG. 4 illustrates a first data record 402 and a second data record 404, where the first and second data records 402/404 are data records of a received dataset (e.g., dataset 305). Each of the first and second data records 402 and 404 is illustrated in FIG. 4 as a line graph showing values of a data statistic for a user (y-axis) collected over a period of time (x-axis). The first data record 402 contains missingness 410 over certain time periods, shown in FIG. 4 as gaps in the line graph. In addition, in some embodiments, the second data record 404 may also contain some amount of missingness 412, where the missingness 412 of the second data record 404 is different from the missingness 410 of the first data record 402.

The missingness dataset processing module 220 uses the missingness of the first data record 402 to mask the second data record 404 to generate a masked second data record 406, e.g., by overlaying the missingness of the first data record 402 onto the second data record 404. The masked second data record 406 includes missingness over time periods corresponding to that of the first data record 402 combined with the original missingness of the second data record 404. The second data record 404 and the masked second data record 406 are included as part of a training dataset (e.g., training dataset 310) used to train a missingness ML model.

The missingness dataset processing module 220 may use different techniques in selecting the first data record 402 and the second data record 404 when generating the training dataset 310 by using the missingness of the first data record 402 to mask the second data record 404. In some embodiments, the missingness dataset processing module 220 generates the training dataset 310 by applying the missingness of each data record of the dataset 305 to a next data record of the dataset, e.g., apply missingness of the first data record to the second data record, apply missingness of the second data record to the third data record, and so forth. In some embodiments, this process is repeated over a plurality of iterations, where the missingness of each data record is applied to a different data record of the dataset during each iteration, to generate the training dataset 310. This mapping of the missingness of each data record to a plurality of other data records of the dataset may be performed to smooth out differences in the behavior of different users corresponding to the different records and overlap between the missingness of different data records.

In some embodiments, the missingness dataset processing module 220, when generating the training dataset 310, analyzes pairs of data records of the dataset 305 when generating the training set 310, to select first and second data records where the missingness of the first data record is suitable to being used to mask the second data record. For example, it may not be useful to use the missingness of the first data record 402 to mask the second data record 404 if the missingness of the second data record was substantially similar to that of the first data record because doing so may reduce the amount of ground truth available to train the SSL model. As such, in some embodiments, the missingness dataset processing module 220 may the missingness of the first data record 402 to mask the second data record 404 only if an amount of overlap between the missingness of the first data record and the second data record does not exceed a threshold amount (e.g., over 20% overlap).

In some embodiments, the missingness dataset processing module 220 determines a level of similarity between the first and second data records and uses the missingness of a first data record to mask a second data record if the level of similarity meets a threshold amount or falls within a range. For example, the first data record may be used to mask the second if they are 60-80% similar but may not be used to mask the second if they are 100% similar or 50% similar. In some embodiments, the level of similarity between the first and second data records may be based upon one or more of a time period during which the physical statistic data of the data records was collected, demographic information associated with the users corresponding to the data records, a level of similarity between values of the physical statistics reflected in the data records, or some combination thereof. For example, in some embodiments, the missingness dataset processing module 220 analyzes the first data record 402 and the second data record 404 to determine a level of correlation between the data of the first data record 402 and the second data record 404 and may use the missingness of the first data record 402 to mask the second data record 404 if the level of correlation is at least a threshold amount.

In some embodiments, the missingness dataset processing module 220 divides the dataset 305 into a plurality of groups, using one or more segmentation or clustering techniques, where missingness of each data record is only used to mask other data records within the same segment or cluster when generating the training dataset 310. In some embodiments, the dataset 305 is segmented or clustered based on demographics information associated with the users corresponding to the data records of the dataset 310, similarity between the values of the data records, or some combination thereof.

In some embodiments, where the first data record 402 and the second data record 404 correspond to different time periods, the missingness dataset processing module 220 may overlay the missingness of the first data record to mask the second data record responsive to a determination that the time periods being overlaid exhibit at least a threshold level of similarity For example, weekend days of different weeks during the same season or the same month may be sufficiently similar, while weekend days of different weeks during different seasons may not be. In some embodiments, missingness of the first data record corresponding to weekends may be applied to mask data of the second data record collected on weekends, but not to mask data of the second data record collected on weekdays, and vice versa.

The missingness dataset processing module 220 uses the training dataset 310 to train a missingness ML model, e.g., where the missingness ML model attempts to predict imputed data for each of the masked data records of the training set 310, the results of which are compared to the corresponding unmasked data records to train the missingness ML model 315.

The second data record 404 and the masked second data record 406 are included as part of a training dataset (e.g., training dataset 310) used to train a missingness ML model, where the missingness ML model is configured to predict imputed data to fill in the missing portions of the masked second data record 406, the results of which are compared to the data of the second data record 404 to train the model. The trained missingness ML model 315 is stored in the missingness ML model store 235.

In some embodiments, the self-supervised learning system may be trained to impute masked data from data records provided by wearable device sensors. The learned representations generated as part of this imputation task may then be used to perform other downstream tasks (e.g., regression or classification).

In some embodiments, the trained model 315 receives a dataset 320 comprising data records having missingness, which may include data records from the dataset 305 and/or different data records, and is fine-tuned (e.g., by using learned representations from the trained model 315 and adapting them to dataset 320) on the new data to fill in the missing portions of the data records of dataset 320 to generate an imputed dataset 325. For example, the trained model may receive a new data record, then generate an imputed data record 408 comprising the original data of the new data record combined with imputed data 414 filling in the missing portions of the new data record.

In some embodiments, the trained model may receive a dataset comprising data records having missingness, which may include data records from the dataset 305 and/or different data records. The model may be fine-tuned (e.g., by adapting the learned representations from training) to a new dataset. The new dataset may include labels. The model may then be able to solve a different ML task, such as detecting an acute illness (e.g., flu onset) from wearable data.

Although FIG. 3 illustrates a single missingness ML model 315, it is understood that in some embodiments, the missingness dataset processing module 220 may train multiple missingness ML models 315. For example, in some embodiments, where the missingness dataset processing module 220 divides the dataset 305 into a plurality of segments or clusters, instead of training a single "universal" missingness ML model, the missingness dataset processing module 220 generates a separate training dataset 310 corresponding to each segment or cluster and trains a different missingness ML model using each different training dataset 310.

In some embodiments, the missingness dataset processing module 220 is configured to train an individual missingness ML model customized to a particular user. For example, in some embodiments, the missingness dataset processing module 220, responsive to receiving a first set of data records corresponding to a first user, identifies a second set of data records of users having at least a threshold level of similarity to the first user, and uses missingness of the first set of data records to mask data records of the second set of data records to generate a training set for training the individual missingness ML model. In some embodiments, missingness of data records of the first set may also be used to mask other data records of the first set, provided that time periods corresponding to the missingness and the data being masked exhibit at least a threshold level of similarity.

In addition, although FIG. 4 illustrates the first and second data records 402 and 404 as representing a single data statistic, it is understood that in some embodiments, data records for a user may include multiple types of data (e.g., different data statistics collected by different types of sensors). For example, as discussed above, data collected for a particular user may include various data statistics such as RHR, step count, time spent active, sleep time, or any combination thereof.

In some embodiments, a particular data record may be missing data for certain data statistics over a time period, while still containing data for other data statistics (e.g., due to the user deactivating or not being in possession of a particular sensor). The missingness dataset processing module 220, when pairing data records to generate the training dataset, may select a second data record based on a level of similarity to the first data record with regards to one or more different data statistics for which masking is to be performed. For example, in a scenario where a first data record contains data for a first data statistic over a given time period but is missing data for a second data statistic (e.g., due to the user not being in possession of a wearable sensor for measuring data for the second data statistic), the missingness dataset processing module 220 may select a second data record having data for the first data statistic that meets a threshold level of similarity to that of the first data record, and mask the data for the second data statistic for the second data record, to train a missingness ML model to impute data for the second data statistic. This may be due to an expectation that the first data record would exhibit similar characteristics with regards to the second data statistic as the second data record, given the similarity of the first and second data records with regards to other metrics.

In some embodiments, the learned representations from the missingness ML model 315 are used for the downstream task of predicting expected data statistic values for a future time period.

In some embodiments, the representations from the missingness ML model 315 can be used to generate synthetic data based on existing data records. By fine-tuning on data records associated with users having certain attributes, the missingness ML model may be able to generate synthetic data that exhibits properties and attributes similar to real data collected from real users, but which is not associated with any identifiable information from real individuals. Synthetic data can be used for privacy, stress testing data pipelines, balancing and augmenting datasets, and removing bias. For example, in some embodiments, a self-supervised learning system may be used to generate realistic synthetic activity data with optional survey data. Because the synthetically generated data is not associated with a real user, this data is not limited by privacy constraints and can be used to test various systems and data pipelines, e.g., for engineering robustness and analytical rigor.

In some embodiments, the representations from the missingness ML model 315 may be used to estimate the burdens (e.g., lost mobility) faced by users due to illness (e.g., flu, coronaviruses such as SARS-CoV-2, i.e., COVID-19). For example, the system may use machine learning to estimate a number of steps a user may have walked normally had that user not suffered an illness-borne loss of mobility. This is further described in U.S. application Ser. No. 16/926,510 (SENSOR-BASED MACHINE-LEARNING IN A HEALTH PREDICTION ENVIRONMENT) and published here: https://jamanetwork.com/journals/jamanetworkopen/fullarticle/2792216.

The disclosed system may be used to detect outliers and anomalies. In some embodiments, the representations from the missingness ML model 315 may enable a downstream ML task to forecast physiological or behavioral data that it may receive about an individual during a future time period. Then, as time passes, the system may detect whether the actual physical or behavioral data it receives matches the forecast, or whether anomalies are present in the received data when it is compared to the forecasted data. This anomaly detection may be applied to multiple individuals to determine whether physiological or behavioral data for a single individual is anomalous when compared to that of a larger population (e.g., members of the same demographic group, for example, for age, sex, race, height, weight, income, or location).

Self-Supervised Learning

The fine-tuning module 240 is configured to fine-tune (train) the learned representations from the self-supervised ML training model. The fine-tuned models may be stored in the fine-tuned ML model store 245, and used to solve the downstream task the model has been fine-tuned on. As discussed above, in self-supervised learning, data records are received by the self-supervised ML model without accompanying labels. Instead, the self-supervised ML model, through analysis of large quantities of input data records, learns how to generate informative representations of the input data records directly from the data records, which then need to be fine-tuned to new tasks, supervised or unsupervised ones. These learned representations after fine-tuning may then be used by the learned representation analysis module 250 for various downstream tasks, such as trend/outlier detection, prediction (e.g., predicting if a user associated with data records with specific learned representations is exhibiting a particular health condition, such as the flu, low sleep, etc.), and/or segmentation (e.g., analyzing the learned representation of user data records to segment a population of users into groups of similar users).

By masking input data based on natural missingness, the self-supervised learning system can improve the quality of learned representations created by the self-supervised ML models, which may translate into improved accuracy in downstream applications performed by the learned representation analysis module 250. In addition, in some embodiments, learned representations from the missingness ML model may be used to provide counterfactual data for comparison actual observed data, e.g., generating synthetic data indicative of healthy days for a particular user, to be compared with observed days during which the user has the flu, to estimate a flu burden amount.

In some embodiments, using a model pre-trained with self-supervised learning may improve classification and regression performance as compared to a traditional approach of supervised training from scratch. For example, using a pre-trained model, model performance on low sample size studies may be improved. In addition, models pre-trained using self-supervised learning are more robust to datasets with label noise, such as in self-reported labels. For example, in some embodiments, self-supervised learning may be used to fine-tune a pre-trained model on wearable sensor data to classify a rare disease that is difficult to recruit for, identify groups of user that have/are about to develop chronic conditions (e.g., diabetes, cardiovascular disease, hypertension, dyslipidemia, sleep apnea, etc.), perform event detection (e.g., ILI/Flu/COVID-19, Migraine, chronic obstructive pulmonary disease (COPD) exacerbation, asthma exacerbation, pregnancy, period tracking, surgery recovery, etc.), and/or generate personalized recommendations (e.g., by calculating actions that would give the participant an optimal trajectory towards a healthier lifestyle).

In some embodiments, extracted features and learned representations generated by a self-supervised ML model may be used cluster and segment received data records (e.g., by users or days), allowing for a health system (e.g., health system 140) to search for similar (or dissimilar) users or days, detect trends and outliers in health and behavior, and/or distill and visualize complex time series datasets to build understanding and identify issues. For example, in some embodiments, learned representations of time series data for individual users may be plotted using a 2 dimensional scatterplot, to visualize the various clusters of behavior, health, and wellness. The scatterplot may be animated over time to visualize how the points trend.

In some embodiments, segmentation or clustering techniques are used to identify population-level groupings and relate them to seasonal changes (e.g., flu season) or track large scale health events (e.g., COVID-19 pandemic). Additionally, each cluster may be mapped to characteristics (e.g., demographics characteristics such as gender, age, body mass index (BMI), etc., health labels such as diabetes, asthma, etc.), to identify activity clusters related to these characteristics, and/or alert users associated with the characteristics of identified changes in their health statuses. In some embodiments, segmentation/clustering techniques may be used to search for a user's "digital twin," e.g., another user whose health, activity, and/or behavioral data closely resembles that of the user. The system may use the "digital twin" feature to match participants in a clinical health study or trial, to provide personalized health insights to similar users, or facilitate health or wellness-related online communities. The "digital twin" feature may even improve the self-supervised learning process. For example, in some embodiments, the missingness dataset processing module 220 may train the self-supervised learning model by using a pattern of missing data of a first digital twin's record to mask the second digital twin's record.

EXAMPLE PROCESSES

FIG. 5 is a flowchart illustrating an example process 500 for performing self-supervised learning using data records having missing data, in accordance with an embodiment. In a first operation 510, a self-supervised learning system may gather a set of data records reflecting physiological or behavioral data from sensor-based monitoring of a plurality of users of wearable devices. The data in the data records may be incomplete for periods when the wearable devices were inactive or not in use.

In a second operation 520, the self-supervised learning system may generate a training data set by using patterns of missing information (i.e., "missingness") in some of the data records of the set to mask other records of the set. For example, in some embodiments, the self-supervised learning system applies a missingness of each data record of the set to a next data record of the set, and repeats the process over one or more iterations to generate the training set. In other embodiments, the self-supervised learning system identifies pairs of data records of the set based a level of similarity and/or a level of overlap in missingness, and applies the missingness of a first data record of the pair to a second data record of the pair to generate the training set.

The self-supervised learning system may train 530 a missingness ML model using the training dataset, where the missingness ML model is trained to generate learned representations from the masked input data records. The missingness ML model may comprise a representation learning backbone (e.g., comprising one or more linear, convolutional, recurrent, self-attention, or transformer layers, or a combination thereof) and a missing data imputation task head (e.g., made up of several pooling, flattening, convolutional, self-attention or fully-connected layers which may feed an output layer the size of the number of input sensor channels to be imputed). Such a model can be trained by minimizing a loss or distance measure (e.g., mean-squared error (MSE) or log-loss) over the output channels over several epochs (or iterations) where the model weights are optimized over data generated by the missingness dataset processing module until a convergence condition (e.g., a satisfactory validation set loss) has been achieved. Training the representation learning backbone to recover the masked values via the missing data imputation task may allow the model backbone to learn general representations of time-series sensor data (e.g., representing one week or month of a subject's health sensor data as a compact numeric representation—e.g., a 256 length float-valued vector). Such compact representations may have multiple downstream applications such as enabling compact, rich feature storage of large time-series databases for fast search, retrieval, and comparison while also allowing the model weights to be reused for new prediction tasks via fine-tuning (e.g., by swapping out the task head and retraining the model for a new task).

The self-supervised learning system uses the learned representations to fine-tune itself to perform downstream tasks. For example, the self-supervised learning system may extract, for each data record, a learned feature representation of the data record, which may be used for additional downstream applications, such as identifying trends and/or outliers among data gathered across a large population, predicting health conditions, segmenting or categorizing data corresponding to different users, imputing missing data, and/or the like.

Figure 6:
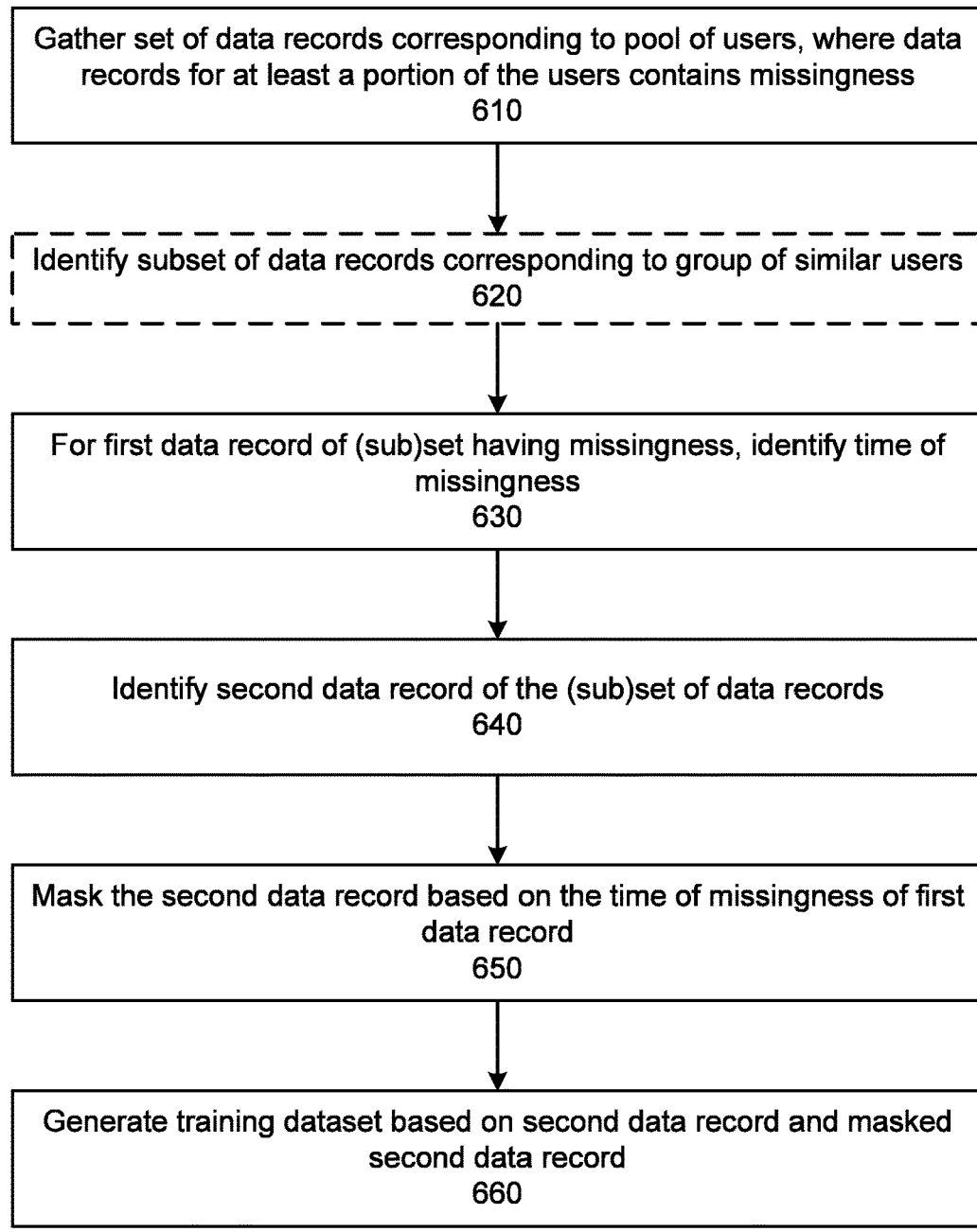
FIG. 6 is a flowchart illustrating an example process for generating a training dataset for training a model to impute missing data of received data records, in accordance with an embodiment.

FIG. 6 is a flowchart illustrating an example process 600 for generating a training dataset for training a model to impute missing data of received data records, in accordance with an embodiment. This learned representation may then be used in the downstream task of imputing missing data of received data records, according to an embodiment. The process 600 of FIG. 6 begins when a self-supervised learning system gathers 610 a set of data records corresponding to a pool of users, where data records for at least a portion of the users contains missing data.

The self-supervised learning system may optionally identify 620 one or more subsets of data records of the pool of data records corresponding to groups of similar users. In some embodiments, the self-supervised learning system identifies the subset of data records using a segmentation or clustering technique.

The self-supervised learning system identifies 630, for a first data record (of the pool of data records or of an identified subset) that contains missingness, a time period corresponding to the missingness of the first data record. The self-supervised learning system identifies 640 a second data record of the pool of data records or of an identified subset. In some embodiments, the self-supervised learning system identifies the second data record based on a level of similarity to the first data record, which may be based on attributes of the users corresponding to the first and second data records, data values of the second data record compared to the first data record, a time period covered by the second data record compared to the first data record, and/or the like, or some combination thereof. In addition, the second data record may be identified based upon an amount of overlap between a missingness time period associated with the second data record and the identified time period of missingness of the first data record. The self-supervised learning system masks 650 the second data record based upon the time period corresponding to the missingness of the first data record. The self-supervised learning system generates 660 the training dataset based on the second data record and the masked second data record.

Figure 7:
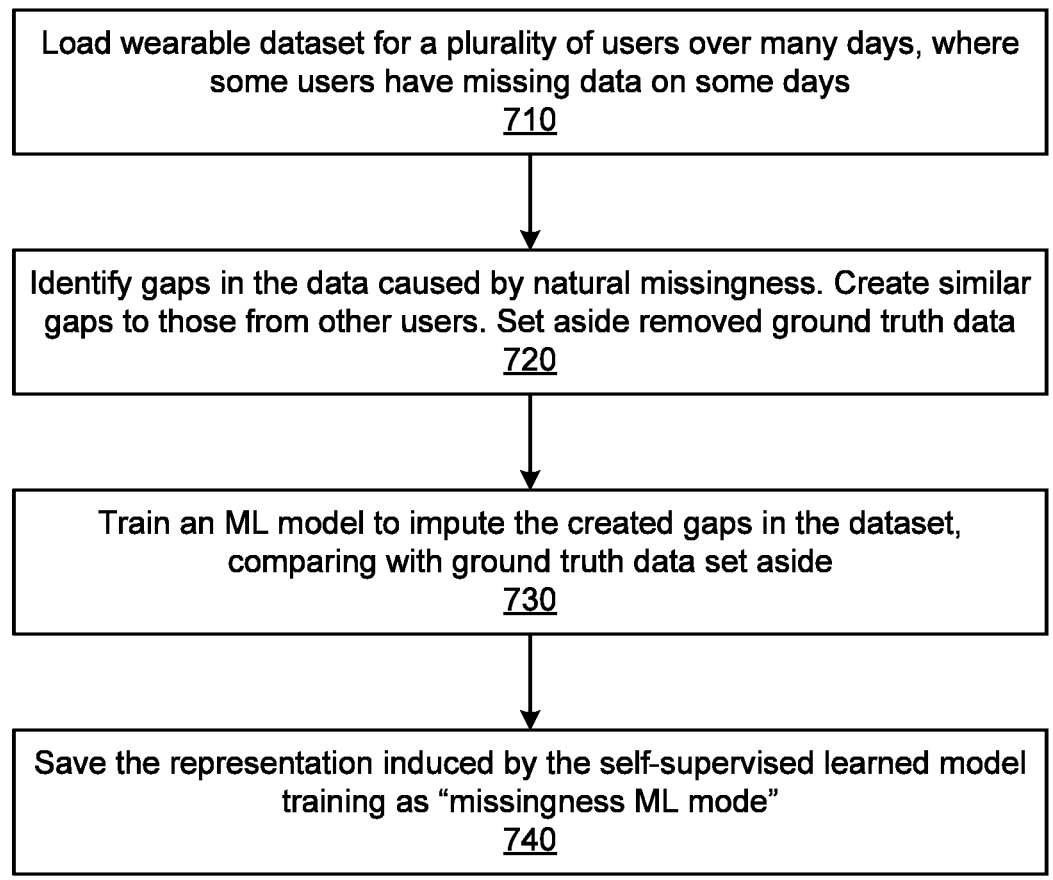
FIG. 7 is a flowchart illustrating an example process for generating learned representations from masked natural missingness data, in accordance with an embodiment.

FIG. 7 is a flowchart illustrating an example process 700 for generating learned representations from masked natural missingness data, in accordance with an embodiment. The learned representations may be used for downstream ML tasks (e.g., imputation, regression, or segmentation). In a first operation 710, the system may load a dataset comprising wearable device data for a plurality of users over a duration (e.g., a period of days, weeks or months). Some users may have missing data for at least some time periods within the duration (e.g., during periods of disuse of the wearable device).

In a second operation 720, the system may identify gaps in the collected wearable data likely caused by natural missingness (naturally-occurring patterns of missing wearable device data). These patterns may be present due to patterns of wearable device disuse or downtime that may occur over a duration of typical use by a subject. Upon determining these patterns, the system may mask one or more portions of data collected from a subject, creating gaps to make the data appear similar to subject data with patterns of natural missingness.

In a third operation 730, the system may train an ML model to impute the created gaps from masking. Training may proceed in several iterations, comparing the imputed dataset to a ground truth until a convergence condition is reached with respect to minimizing a loss or cost function. This training process may produce learned representations from the data. These learned representations may be lower-dimensional modifications or transformations of the data which may comprise essential features to describe the data. For example, learned representations may be compressed forms of data, which may have non-essential features removed.

In a fourth operation 740, the system may retain the learned representations generated from this process. These retained representations may be used for downstream tasks.

Figure 8:
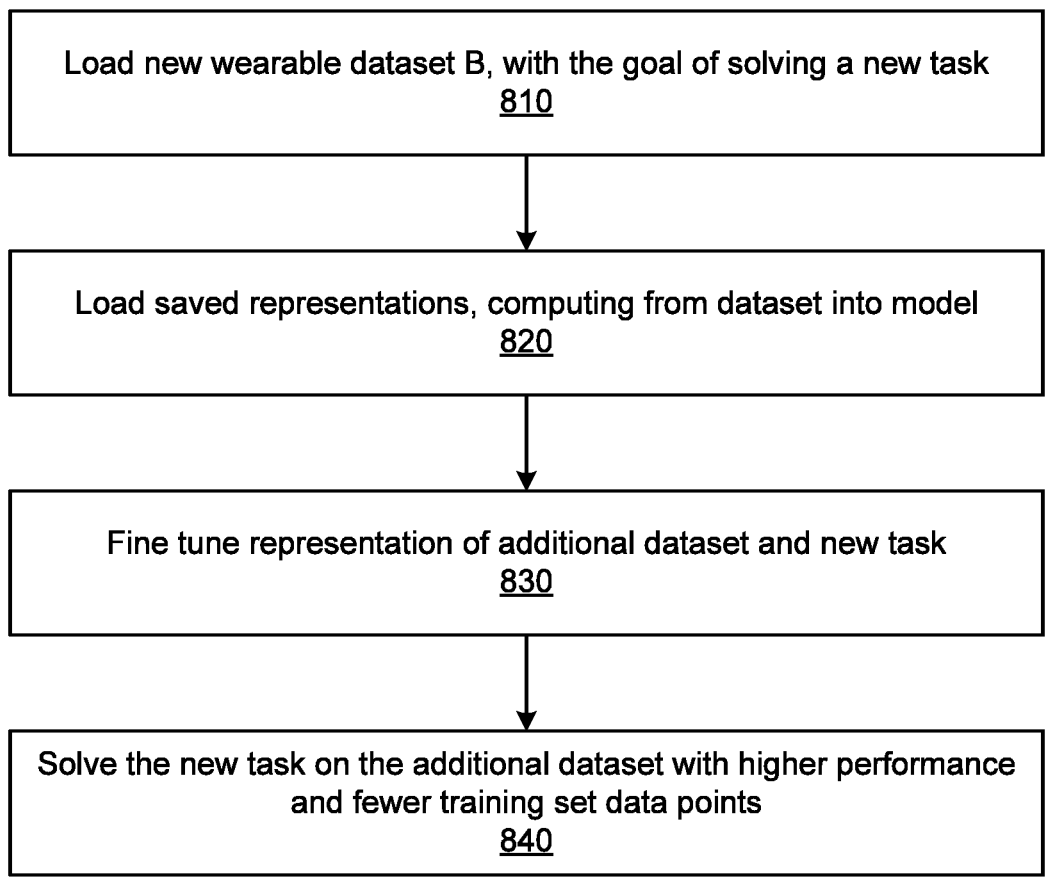
FIG. 8 is a flowchart illustrating an example process for computing a downstream task once learned representations have been determined through training, in accordance with an embodiment.

FIG. 8 is a flowchart illustrating an example process 800 for computing a downstream task once learned representations have been determined through training (i.e., in operation 740), in accordance with an embodiment. In a first operation 810, the system may receive a wearable device dataset and be provided with a downstream task to solve. The downstream task may be, for example, representation, segmentation, or regression.

In a second operation 820, the system may retrieve a pretrained ML system (i.e., from operation 740) that has generated learned representations based at least in part on imputing masked data.

In a third operation 830, the system may provide the wearable device data to the machine learning model, to fine-tune the learned representation models with respect to the new data that has not been used to train the ML algorithms and/or models in the system.

In a fourth operation 840, the system may provide the fine-tuned learned representations to a machine learning sub-system to solve the new task.

In some embodiments, the system may use the pretrained model for downstream tasks without computing the learned representations. The system may train the model to impute masked data. Then, the weights from the training may be used to solve a downstream task.

EXAMPLES

In one embodiment, the system may predict a subject's age from collected wearable data. A time series transformer (TST) architecture may ingest wearable data (e.g., daily resting heart rate (RHR), sleep duration, and total steps walked) and predict an age of a subject. Prior to predicting the age, the system may first generate learned representations by imputing masked data, as described elsewhere in this disclosure (e.g., in process 700). The system may leverage a large database of pairs (e.g., <wearable time series data, age>) and then may use a subset of the pairs for model training and validation and a different subset for testing.

An experiment using a pre-trained TST with learned representations derived from imputing data from natural missingness masking observed a substantial improvement in predictive power over use of a non-pretrained TST. For example, as shown in Table 1, the pre-trained TST produced a 5.30% decrease in mean absolute error, and 37.14% improvement in correlation of the age prediction with the ground truth.

TABLE 1

|  | Pre-trained TST | TST | Improvement % |
|---|---|---|---|
| MAE (lower is better) | 7.5 | 7.92 | −5.30% |
| Correlation (higher is better) | 0.48 | 0.35 | 37.14% |

Figure 9:
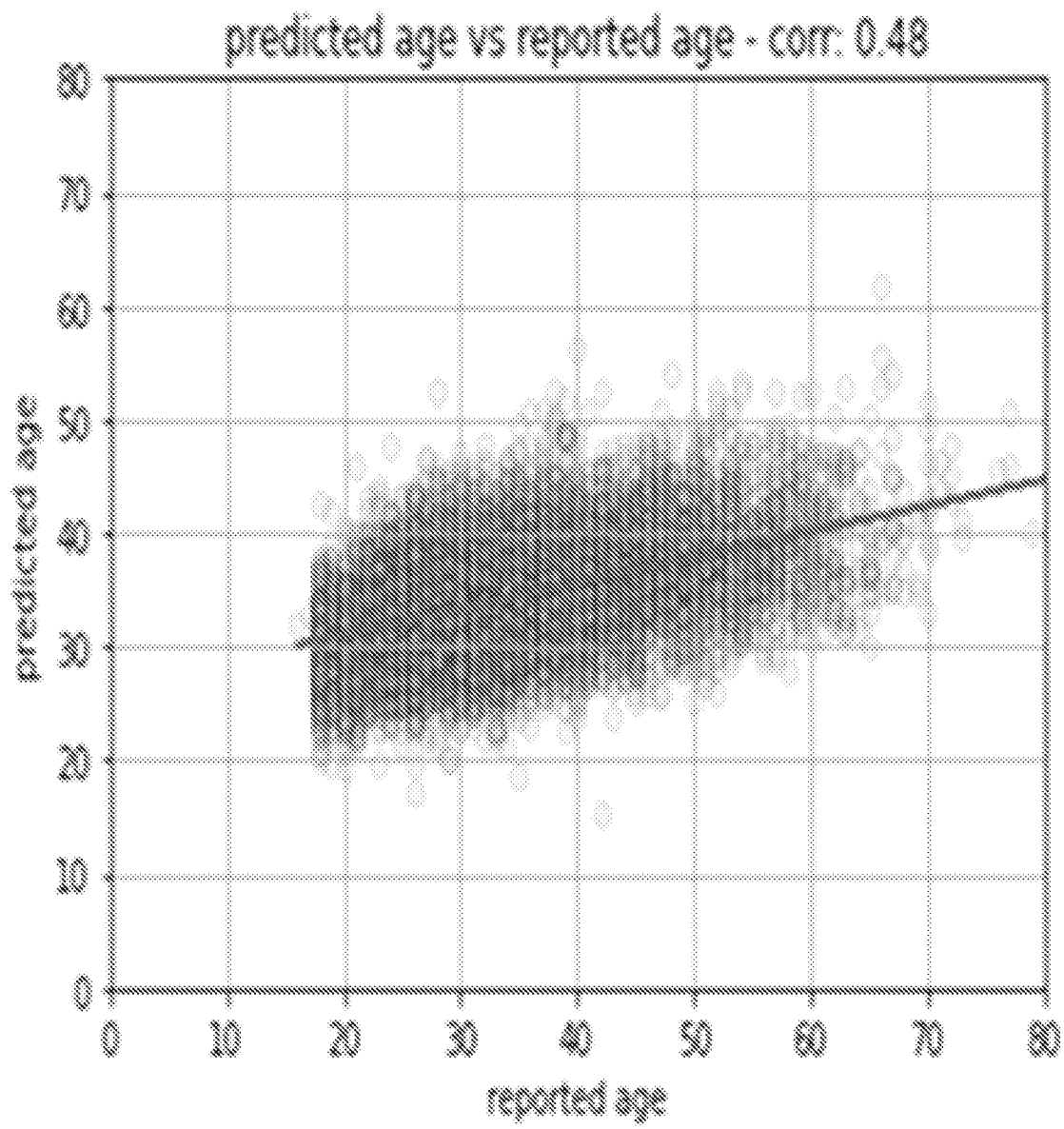
FIG. 9 shows experimental results comprising a plot of the correlation of an age prediction and a reported ground truth age.

FIG. 9 shows experimental results comprising a plot of the correlation of the age prediction and the reported ground truth age. The plot shows a correlation of 0.48 between the predicted age and the reported age. This correlation may be visualized as the slope of a best fit line or trendline through a set of <reported age, predicted age> pairs.

The learned representations generated using the methods disclosed may be used downstream to predict influenza-like-illness (ILI) from wearable data using, for example, a Time Series Transformer architecture (TST).

In this experiment, the model was pre-trained on minute-level wearable data, including heart rate, sleep, and step count, and identified 36-70% more ILI positive members on their first day of symptoms than a day-level TST model without self-supervised pre-training. Results are summarized in Table 2.

TABLE 2

|  | Pre-trained TST | TST | Improvement % |
|---|---|---|---|
| Lift New Users (higher is better) | 10.6 | 7.8 | 35.9 |
| Lift Existing Users (higher is better) | 18.8 | 11.1 | 69.37 |

Figure 10:
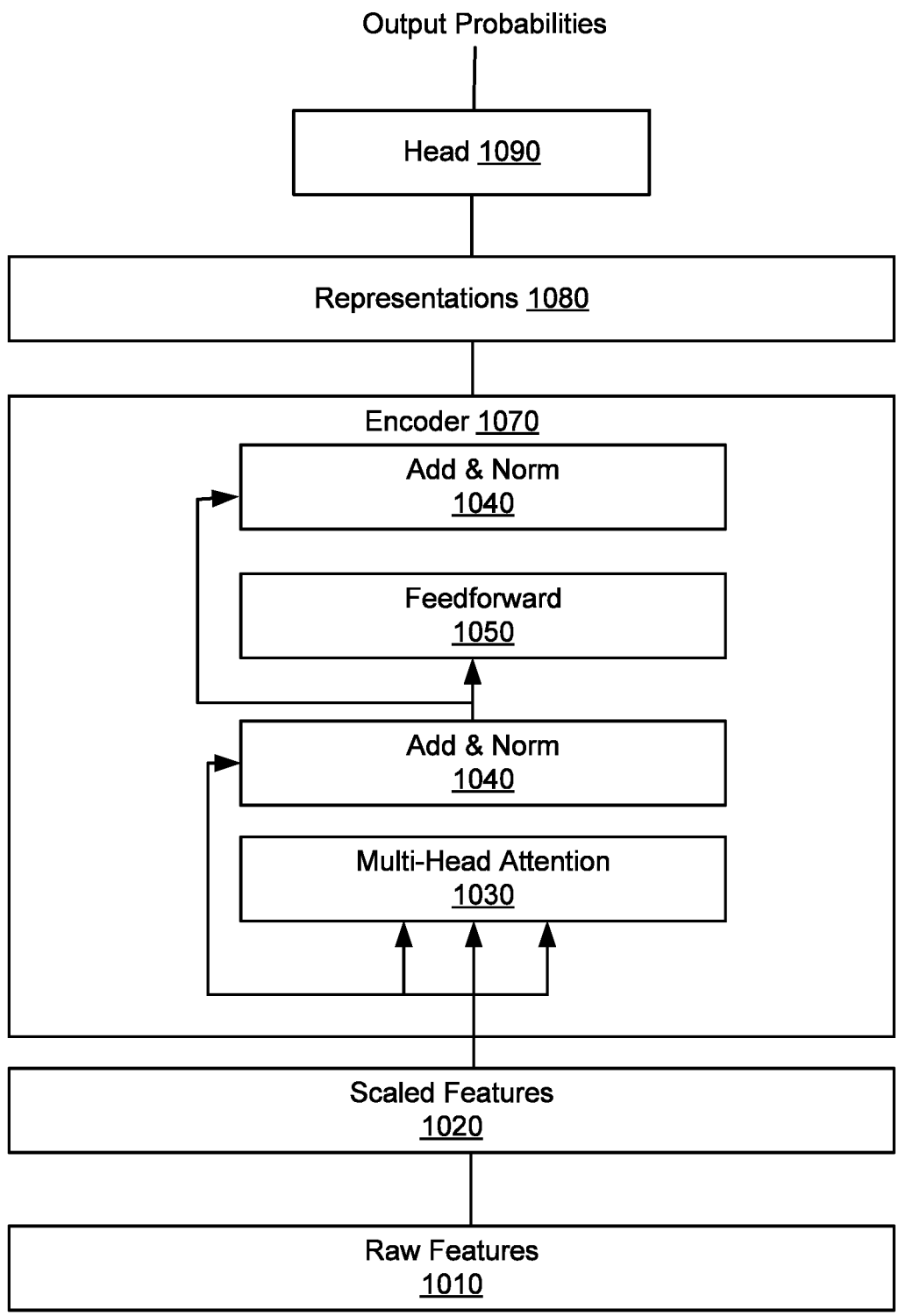
FIG. 10 illustrates a machine learning architecture used for applying natural missingness masking to a downstream machine learning prediction task, in accordance with an embodiment.

FIG. 10 illustrates a machine learning architecture 1000 used for applying natural missingness masking to a downstream machine learning prediction task (e.g., age prediction in the preceding example), in accordance with an embodiment. FIG. 10 illustrates raw features 1010, scaled features 1020, an encoder 1070, representations 1080, and a head 1090.

The raw features 1010 may be collected by a wearable device. The raw features 1010 may be collected over a period of days, weeks, months, or years. For example, the features may be collected over a period of less than one week, less than two weeks, less than three weeks, less than four weeks, less than five weeks, less than six weeks, less than seven weeks, less than eight weeks, less than 10 weeks, less than 12 weeks, less than 16 weeks, less than six months, or less than one year. For example, the features may be collected over a period of more than one week, more than two weeks, more than three weeks, more than four weeks, more than five weeks, more than six weeks, more than seven weeks, more than eight weeks, more than 10 weeks, more than 12 weeks, more than 16 weeks, more than six months, more than one year, or greater. The features may be collected over a period of between one and two weeks, between two and four weeks, between one and two months, between two and three months, between three and six months, or between six months and one year.

The raw features 1010 may be time series wearable sensor data. The time series data may be collected at a frequency of at least once every microsecond, at least once every millisecond, at least once every second, at least once every ten seconds, at least once every 30 seconds, at least once every minute, at least once every five minutes, at least once every 10 minutes, at least once every 15 minutes, at least once every 30 minutes, at least once every 45 minutes, at least once every hour, at least once every two hours, at least once every three hours, at least once every six hours, at least once every 12 hours, at least once a day, at least once a week, at least biweekly, at least triweekly, at least monthly, at least every two months, at least twice a year, or at least once per year. The raw data may be collected at a frequency of at most once every microsecond, at most once every millisecond, at most once every second, at most once every ten seconds, at most once every 30 seconds, at most once every minute, at most once every five minutes, at most once every 10 minutes, at most once every 15 minutes, at most once every 30 minutes, at most once every 45 minutes, at most once every hour, at most once every two hours, at most once every three hours, at most once every six hours, at most once every 12 hours, at most once a day, at most once a week, at most biweekly, at most triweekly, at most monthly, at most every two months, at most twice a year, or at most once per year. The raw data may be collected between once per microsecond and once per millisecond, between once per millisecond and once per second, between once per second and once per ten seconds, between once per ten seconds and once per 30 seconds, between once per 30 seconds and once per minute, between once per minute and once per ten minutes, between once per 10 minutes and once per 30 minutes, between once per 30 minutes and once per hour, between once per hour and once per two hours, between once per two hours and once per six hours, between once per six hours and once per 12 hours, between twice a day and once a day, between once a day and once a week, between once a week and once every two weeks, between once every two weeks and once every month, between once every month and once every two months, between once every two months and once every six months, or between once every six months and once a year.

In some embodiments, all types of raw data are collected at the same frequency. In some embodiments, at least one type of raw data is collected at a different frequency than another type of raw data.

In the embodiment of FIG. 10, the raw wearable device data has dimensionality of 7×10080, for data collected every minute for seven weeks.

The raw features 1010 may be converted into scaled features 1020. The scaled features 1020 may be features of a different time series than the raw data. The scaled features 1020 may be features binned at a larger time scale than those of the raw features. For example, if the raw features are collected every minute, the scaled features 1020 may convert the raw features to hourly, daily, weekly, or monthly features. The raw features 1010 may be converted to scaled features 1020 using a transformation. The transformation may be a convolution. In the embodiment of FIG. 9, a convolution with a kernel size of 60 and a stride of 60 may produce hourly scaled features from the per-minute raw features.

The encoder sub-system 1070 may generate representations from the data. The encoder sub-system may comprise one or more machine learning algorithms. In some embodiments, one or more of the machine learning algorithms comprises a neural network (or artificial neural network (ANN)). A neural network may be a convolutional neural network (CNN) or recurrent neural network (RNN). A neural network may be a multilayer perceptron (MLP).

In some embodiments, the encoder sub-system 1070 may resemble a transformer encoder. In some embodiments, the encoder may include a multi-head attention layer, the output of which is normalized by one of the addition and normalization (add and norm) layers 1040, which is fed to a feedforward neural network (e.g., an MLP), the output of which is again normalized.

In some embodiments, the encoder sub-system 1070 may comprise an attention mechanism. The attention mechanism may be a self-attention mechanism. The attention mechanism may be a multi-head attention mechanism.

An attention mechanism may project an input set of features into query, key, and value vectors. The attention mechanism may calculate the dot product of the query and key vectors, which may be indicative of a relationship between the two vectors. Then, the attention mechanism may scale this dot product and then compute the SoftMax of this scaled dot product. Then, the attention mechanism may compute the product of the SoftMax with the value vector. A multi-head attention mechanism may perform the preceding calculations with respect to many different query, key, and value vectors.

The feedforward network 1050 may process the normalized output of the multi-head attention mechanism. This may configure the representation to be an input to another type of machine learning system (e.g., one used to perform a downstream task). The feedforward network may comprise one or more neural network layers. The feedforward network may be an MLP.

The representations 1080 may be modifications or transformations of the features that are produced when the scaled features 1020 are processed by the encoder 1070. The representations 1080 may comprise information completely describing the input features, with extraneous or less predictive information removed. For example, the representations may be compressed versions of the scaled features. The representations 1080 may be generated when the encoder 1070 imputes masked data. Masked data portions may correspond to patterns of naturally occurring missing wearable device data, for example, when wearable devices are idle or not in use. The architecture 1000 may fine-tune the representations 1080 on downstream processing tasks, such as imputation, regression, segmentation, or classification tasks. Fine-tuning may comprise further modifying the representations from processing new data (i.e., unseen during training) with the encoder sub-system 1070.

The head 1080 may process the representations 1080 to perform a downstream task. The head 1080 may comprise one or more machine learning algorithms configured to perform the downstream task. For example, the head 1080 may comprise one or more supervised and/or unsupervised machine learning algorithms. The head 1080 may comprise, for example, support vector machines (SVM), a logistic regression, or a decision tree algorithm (e.g., gradient boosted trees, Adaboost, XGBoost, or random forests). The head may comprise one or more layers.

The head 1080 may comprise an activation function to produce a prediction output. The head may perform a regression task. The head may perform a classification task. The head may comprise a binary classifier. The head may comprise a multiclass classifier.

The head 1080 may comprise one or more activation functions to produce a prediction result. For example, the head may comprise a binary step, logistic or sigmoid, tanh, rectified linear unit (ReLU), or Gaussian activation function for a binary classification task. For multiclass problems, the head may comprise a softmax activation function.

In some embodiments, machine learning architectures may have additional or fewer layers.

Synthetic Data Generation

Disclosed herein is a multi-task self-attention model that may generate realistic wearable activity data.

High quality health data may be a vital yet scarce resource in modern healthcare. For many types of machine learning problems, raw data collection may be expensive, difficult, and/or time consuming. Additionally, labeling raw data for supervised learning may require expert knowledge and may be time-consuming. Additionally, privacy concerns may necessitate expensive access control systems to safeguard personal or enterprise data. As a result, most health datasets may fail to capture the true distribution of the underlying population, particularly for individuals who may have data corresponding to tails of human population distributions, who may suffer from rare conditions (e.g., diseases or illnesses) and/or may possess underrepresented attributes (e.g., genetic attributes). Generating unseen, yet realistic instances may mitigate problems in data collection, enabling novel machine learning-based analyses.

For machine learning tasks to be representative, it may be crucial that generated samples remain realistic and reflective of the data intended for study. Generating synthetic data which closely approximates wearable sensor data may be a difficult task and may need to be finely balanced with the requirement to generate new samples instead of simply recreating those seen in the training set. In other fields where data generation is used, the same principle may apply.

Due to the potential high risk of applications in the healthcare field, generating realistic data may be of special concern. This may be an especially significant need given that privacy concerns may limit access to large datasets which would enable training of realistic generative models.

Architecture and Learning

A synthetic data generation machine learning (ML) system may comprise at least a portion of a transformer system. For example, a synthetic data generation ML system may comprise a transformer decoder.

It may be important to preserve positional information of features or data items in a sequence of wearable data. For example, wearable device data values may exhibit periodic variations based on patterns of use or disuse (e.g., over a day or a week). Preserving positional information may comprise assigning and applying weights to features, or to derivatives of the features (e.g., embeddings) that may be processed by the synthetic data generation ML system.

The features or embeddings may be provided to a transformer comprising decoder layers. The decoder layers may comprise a multi-head attention mechanism, such as those described elsewhere in this disclosure. As generating synthetic data may be an autoregressive task, at least a portion of a weight matrix used for attention may be masked. The decoder layers may additionally comprise one or more feedforward neural networks, which may comprise an activation function (e.g., Gaussian error linear units (GeLU), rectified linear units (ReLU), sigmoid, or tanh).

Embodiments of the disclosure may generate synthetic data by iteratively appending wearable data points to the end of a collected sequence of wearable data (e.g., at "future points" in the sequence), while removing non-synthetic (i.e., actually collected by wearable device sensors) values from the front of the sequence. This may be performed until the entire wearable dataset comprises synthetic data.

Embodiments of the disclosure may generate synthetic data by placing synthetic data values in gaps within a collected sequence of wearable sensor data (e.g., at places where data is missing or has been masked), while removing non-synthetic wearable sensor data values. This may be performed until the entire wearable dataset comprises synthetic data.

A fully trained system to generate synthetic wearable data may be able to impute large numbers of wearable data values to a sequence comprising only sparse amounts of non-synthetic wearable data. In some embodiments, a fully trained system may generate a sequence of wearable sensor data from a single "seed" value.

Generating New Samples

To test the model, a time-series set of data, taken from a held-out set, may be input into the trained model. Then, the system may recursively remove data from the first day of the sequence and append next-day predictions to the end.

Experiment

The following are descriptions of experimental setup and results and should not be construed to limit any of the preceding disclosure.

Dataset

All models were trained and evaluated on the same set of activity data acquired during wearable FitBit® trackers. The dataset contained day-level data from 7,500 individuals who gave permission to use their data for the purpose of this work, spanning one year, resulting in a total of 2,737,500 person-days. The data contains three channels: resting heart rate (beats per minute), total sleep (minutes), and total steps (step count).

Pre-Processing

Missing data was imputed with the mean feature values per individual. Each feature was then scaled for [0,1]. The experiment used a sequence length of 21 days. The disclosed system may use sequences shorter than those used with most transformers because every source sequence may be of length 365, corresponding to each day in the year for an individual. The shorter sequence length may give a more diverse set of samples while still capturing a representative time period on the scale of human activity.

Although the labels are continuous values, they were converted to a one-hot encoding of 100 evenly-spaced bins. This was done to model the outputs as a softmax distribution.

Architecture and Learning

Three input channels were embedded in a 64-dimension space through learned embedding weights. As the sequences were temporarily ordered, their positional relationships were preserved. They were positionally encoded with learned positional weights that were added to the embedded inputs.

The embeddings were passed into a transformer comprising decoder layers. The upper right triangle of the attention weight matrix was masked to ensure that future information was not being used.

Each block was computed by a feedforward network of two dense layers of dimensionality 256, with GeLU activation and dropout probability of 0.1 during training. Three of these blocks were stacked to form the core of the model and four attention heads. This was followed by a feed-forward network to an output of three 100-unit vectors, corresponding to the three tasks and 100 bins. A softmax activation function was applied to each one to obtain the logits used for loss calculation. This resulted in a causally-masked multi-head multi-task self-attention model that was trained to model and forecast activity time series.

Loss

The system used a softmax distribution of outputs. Thus, the system minimized the cross-entropy loss between the predicted and true values. The three outputs (resting heart rate, daily steps, and sleep minutes) were learned jointly with separate feed-forward network heads.

Training

The loss was minimized using the Adam stochastic optimization algorithm and an initial learning rate of $10^{-3}$, reducing it by a factor of 10 every 5 epochs, with a total of 15 training epochs.

Generating New Samples

A positionally-encoded data sequence (time series and binned daily) was taken from a held-out set and input into the trained model. Then, the first day of the sequence was recursively removed and the next-day predictions were appended to the end. Scaling the temperature of the logits may give more consistent results for resting heart rate and sleep. Temperatures of 0.3 and 0.7 were used. The three softmax distributions may be sampled independently to obtain the next day value.

Results

Figure 11:
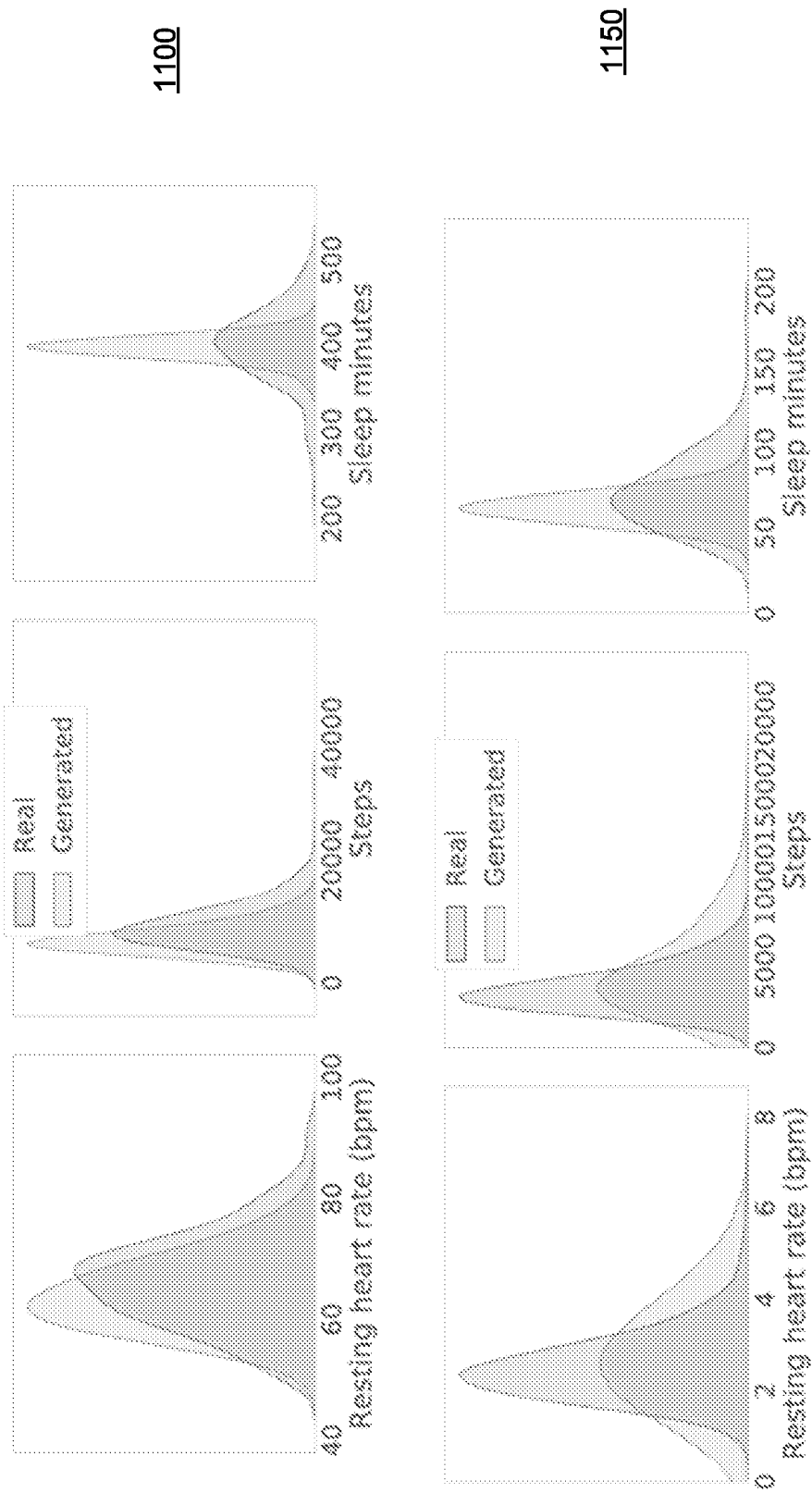
FIG. 11 highlights and compares experimental examples of real and generated activity data across three different channels.

FIG. 11 highlights and compares experimental examples of real and generated activity data across three different channels: resting heart rate, steps taken per day, and minutes spent asleep. This is plotted over three months (120 days) to inspect both short-term and long-term trends. The generated sequences are visually like the real examples. The model may capture the individual properties of the three different modalities. Resting heart rate remains relatively stable without spikes or clear trends. Recorded and generated steps may be highly variable, with differences over orders of magnitude between consecutive days and spikes representing very high-step days.

Plot 1100 shows distributions of individual sequence means. These means inform of the generators ability to produce variation between samples. The results show agreement for both resting heart rate and steps, but the model less frequently produces individuals with very high resting heart rates or step counts. The model may be more conservative when generating sleep minutes, with lower chances of generating samples far from the population mean.

Plot 1150 shows distributions of individual standard deviations. This informs of the generator's capacity to create variation within samples. For all features, the mean of standard deviations may be captured well. But the model may be more likely to create samples with higher variance of resting heart rate and steps, but a lower variance of sleep duration.

Resting heart rate is well-captured by the model with similar time series observed and synthesize. Comparing the distributions of values between plots 1100 and 1150 shows that the model captures a near perfect distribution of individual means. The model is not generating sequences that have means out of the true distribution.

DISCUSSION

The disclosed time series data generator can synthesize realistic resting heart rate, step count, and sleep records. The time-series generator may be controlled to output sequences with highly specific activity data properties.

Synthetic wearable data may have many applications, ranging from study simulation to data visualization and quality control. Personal health monitoring may require significant amounts of data and careful study design. Synthesized data may assist with development and testing of new analysis tools to monitor personal health. Generated data may be modulated to enable testing of edge cases and rare conditions not observed in original real-world cohorts, without generating privacy concerns.

Figure 12:
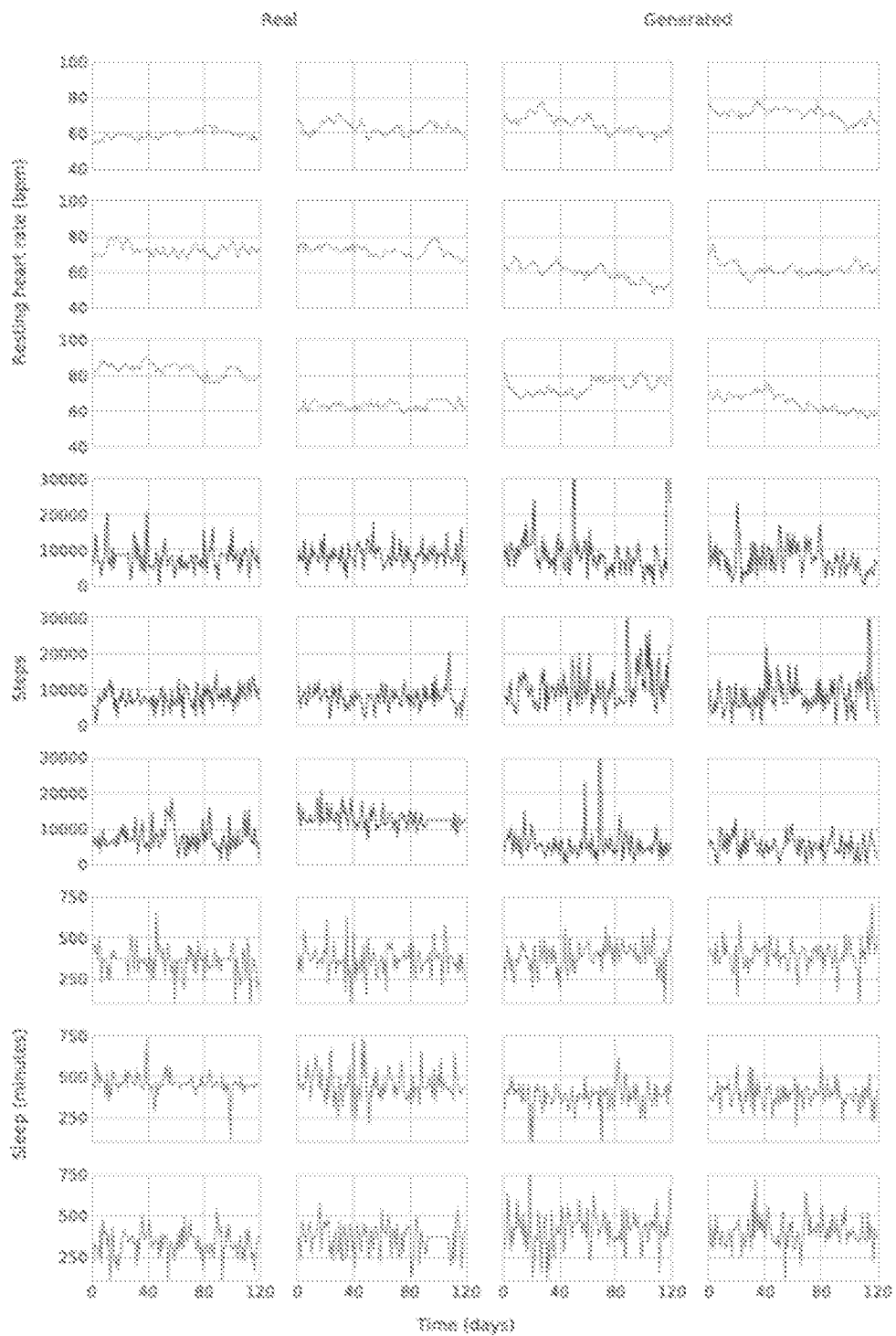
FIG. 12 illustrates experimental results showing a comparison of real and generated wearable activity data.

FIG. 12 illustrates experimental results showing a comparison of real and generated wearable activity data. Each subplot represents data collected for a single individual. The two left columns show real data sequences collected from a wearable FitBit® device. The two right columns show synthetic sequences generated by the model. Resting heart rate is shown in the top three rows, steps taken per day in the three center rows, and total minutes spent sleeping per day in the bottom three rows.

CONCLUSION

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

Computer Systems

Figure 13:
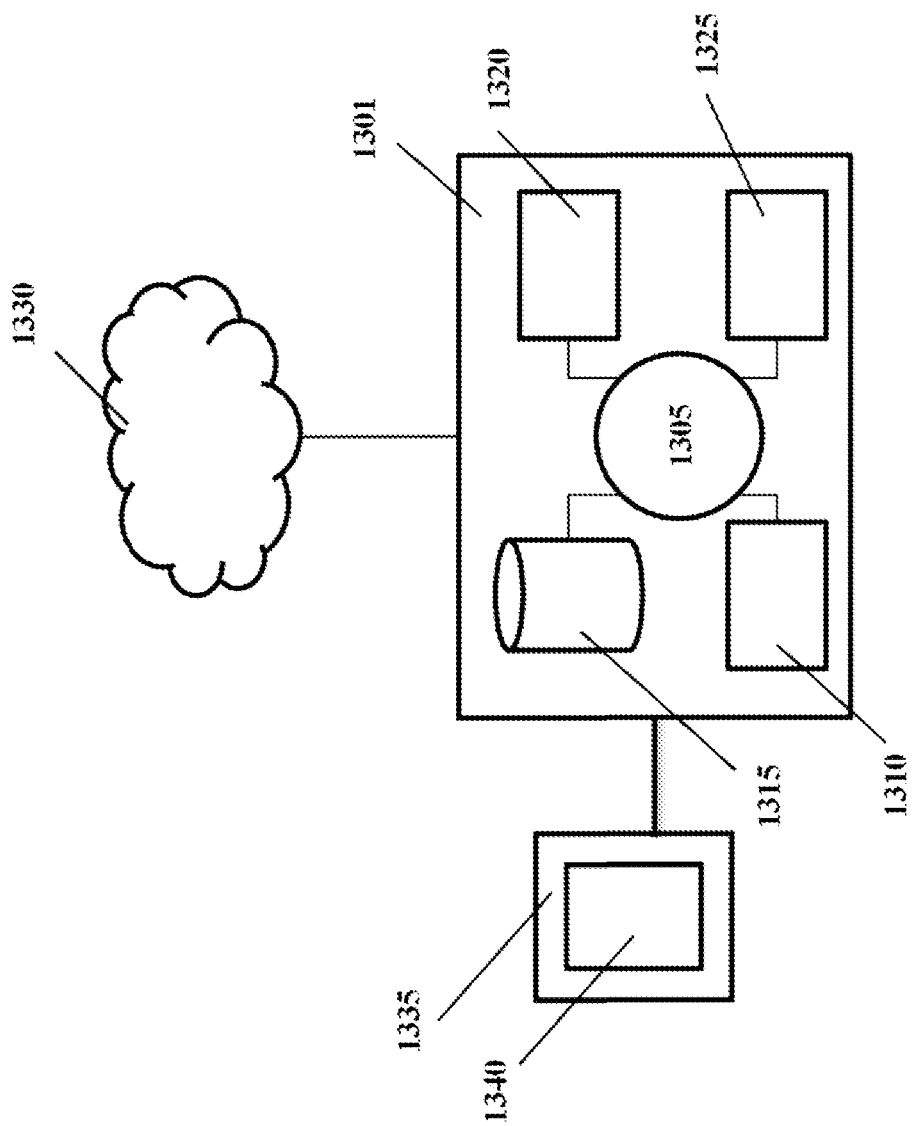
FIG. 13 shows a computer system that is programmed or otherwise configured to implement methods provided herein.

The present disclosure provides computer systems that are programmed to implement methods of the disclosure. FIG. 13 shows a computer system 1301 that is programmed or otherwise configured to implement a self-supervised learning system. The computer system 1301 can regulate various aspects of data collection and machine learning of the present disclosure, such as, for example, generating learning representations of sensor data. The computer system 1301 can be an electronic device of a user or a computer system that is remotely located with respect to the electronic device. The electronic device can be a mobile electronic device.

The computer system 1301 includes a central processing unit (CPU, also "processor" and "computer processor" herein) 1305, which can be a single core or multi core processor, or a plurality of processors for parallel processing. The computer system 1301 also includes memory or memory location 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The computer system 1301 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 1330, in some cases with the aid of the computer system 1301, can implement a peer-to-peer network, which may enable devices coupled to the computer system 1301 to behave as a client or a server.

The CPU 1305 can execute a sequence of machine-readable instructions, which can be embodied in a program or software. The instructions may be stored in a memory location, such as the memory 1310. The instructions can be directed to the CPU 1305, which can subsequently program or otherwise configure the CPU 1305 to implement methods of the present disclosure. Examples of operations performed by the CPU 1305 can include fetch, decode, execute, and writeback.

The CPU 1305 can be part of a circuit, such as an integrated circuit. One or more other components of the system 1301 can be included in the circuit. In some cases, the circuit is an application specific integrated circuit (ASIC).

The storage unit 1315 can store files, such as drivers, libraries and saved programs. The storage unit 1315 can store user data, e.g., user preferences and user programs. The computer system 1301 in some cases can include one or more additional data storage units that are external to the computer system 1301, such as located on a remote server that is in communication with the computer system 1301 through an intranet or the Internet.

The computer system 1301 can communicate with one or more remote computer systems through the network 1330. For instance, the computer system 1301 can communicate with a remote computer system of a user (e.g., a smartphone). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1301 via the network 1330.

Methods as described herein can be implemented by way of machine (e.g., computer processor) executable code stored on an electronic storage location of the computer system 1301, such as, for example, on the memory 1310 or electronic storage unit 1315. The machine executable or machine readable code can be provided in the form of software. During use, the code can be executed by the processor 1305. In some cases, the code can be retrieved from the storage unit 1315 and stored on the memory 1310 for ready access by the processor 1305. In some situations, the electronic storage unit 1315 can be precluded, and machine-executable instructions are stored on memory 1310.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1301 can include or be in communication with an electronic display 1335 that comprises a user interface (UI) 1340 for providing, for example, predictions derived from physical statistics collected from wearables. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1305. The algorithm can, for example, impute missing data into health records.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method comprising:
   (a) identifying, based at least in part on one or more demographics of a target user, a population from a larger group of users, wherein the population comprises one or more digital twins of the target user, and wherein the population is characterized by having a common demographic;
   (b) accessing, by a machine learning system, a set of data records for a plurality of users of the population, the set of data records representative of physical statistics measured for each user of the plurality of users of the population over a time period, wherein the physical statistics for each user of the plurality of users of the population are measured using a wearable device associated with each user of the plurality of users of the population;
(c) generating a set of masked data records by masking at least a subset of the set of data records in accordance with a pattern of missingness from the set of data records, wherein the pattern of missingness from the set of data records corresponds to periods of disuse or deactivation of the wearable device associated with each user of the plurality of users of the population;
(d) generating, by the machine learning system, a plurality of learned representations from at least the set of masked data records; and
(e) fine tuning, by the machine learning system, a machine learning model using the plurality of learned representations, the machine learning model configured to perform a downstream machine learning task that comprises imputing missing data from a wearable device associated with the target user, thereby generating complete data for the target user.

2. The method of claim 1, wherein a data record of the subset of the set of data records comprises missing data different from the pattern of missingness.

3. The method of claim 2, further comprising using a learned representation of the plurality of learned representations to identify another subset of the set of data records using one or more clustering or segmentation techniques to one or more of: (i) perform event detection, (ii) detect or predict onset of an acute health condition, (iii) monitor a chronic health condition, (iv) detect trends, (v) detect outliers, or (vi) identify users that closely resemble one another in terms of health, behavior, or activity.

4. The method of claim 1, wherein generating the set of masked data records comprises determining a level of similarity between a data record of the set of data records and a data record of the subset of the set of data records.

5. The method of claim 1, wherein generating the set of masked data records comprises dividing the subset of the set of data records into a plurality of groups using one or more segmentation or clustering techniques, wherein missingness of each data record of the subset of the set of data records is used to mask another data record of the subset of the set of data records that is within a common group of the plurality of groups when generating a training dataset.

6. The method of claim 1, wherein the physical statistics comprise physiological data, wherein the physiological data comprise one or more of: resting heart rate, current heart rate, heart rate variability, respiration rate, galvanic skin response, skin temperature, or blood oxygen level.

7. The method of claim 1, wherein the physical statistics comprise behavioral data, and wherein the behavioral data comprise one or more of: daily number of steps, distance walked, time active, exercise amount, exercise type, time slept, number of times sleep was interrupted, sleep start times, sleep end times, napping, or resting.

8. The method of claim 1, wherein the set of data records comprise time series data.

9. The method of claim 1, wherein the wearable device associated with each user of the plurality of users of the population comprises a personal health sensor device.

10. A system comprising a computing device comprising at least one processor and instructions executable by the at least one processor to cause the at least one processor to perform operations comprising:
(a) identifying, based at least in part on one or more demographics of a target user, a population from a larger group of users, wherein the population comprises one or more digital twins of the target user, and wherein the population is characterized by having a common demographic;
(b) accessing, by a machine learning system, a set of data records for a plurality of users of the population, the set of data records representative of physical statistics measured for each user of the plurality of users of the population over a time period, wherein the physical statistics for each user of the plurality of users of the population are measured using a wearable device associated with each user of the plurality of users of the population;
(c) for each data record of a subset of the set of data records:
(i) identifying, by the machine learning system, a portion of the time period associated with a pattern of missing data from the set of data records, wherein the pattern of missing data corresponds to periods of disuse or deactivation of the wearable device associated with each user of the plurality of users of the population, and
(ii) generating, by the machine learning system, a masked data record by masking a portion of an additional data record of the set of data records corresponding to the identified portion of the time period, wherein the masking of the additional data record of the subset of the set of data records causes the additional data record to resemble the pattern of missing data;
(d) generating, by the machine learning system, a training dataset comprising both of at least the portion of the additional data record and the corresponding generated masked data record for each data record of the subset of the set of data records;
(e) training, by the machine learning system, a machine learning model using the generated training dataset, the machine learning model configured to predict, for a received data record comprising masked data, imputed data corresponding to data of the received data record obscured based on the masked data;
(e) generating, by the machine learning model, a plurality of learned representations, wherein the plurality of learned representations are associated with the prediction of the imputed data; and
(g) fine-tuning, by the machine learning system, a learned representation of the plurality of learned representations to a downstream machine learning task, wherein the downstream machine learning task comprises processing a set of data records from a wearable device associated with the target user, thereby generating complete data for the target user.

11. The system of claim 10, wherein the additional data record comprises missing data different from the identified portion of the time period of the corresponding data record.

12. The system of claim 10, wherein the instructions are executable by the at least one processor to cause the at least one processor to perform operations further comprising: determining a level of similarity between a current data record and the additional data record.

13. The system of claim 10, wherein the instructions are executable by the at least one processor to cause the at least one processor to perform operations further comprising: dividing the subset of the set of data records into a plurality of groups using one or more segmentation or clustering techniques, wherein the pattern of missing data from the set of data records is used to mask other data records within a common group of the plurality of groups when generating the training dataset.

14. The system of claim 10, wherein the missing data is a result of missingness arising from user behavioral patterns.

15. The system of claim 10, wherein the physical statistics comprise physiological data, wherein the physiological data comprise one or more of: resting heart rate, current heart rate, heart rate variability, respiration rate, galvanic skin response, skin temperature, or blood oxygen level.

16. The system of claim 10, wherein the physical statistics comprise behavioral data, wherein the behavioral data comprise one or more of daily number of steps, distance walked, time active, exercise amount, exercise type, time slept, number of times sleep was interrupted, sleep start times, sleep end times, napping, or resting.

17. The system of claim 10, wherein the set of data records comprise time series data.

18. The system of claim 10, wherein the set of data records are generated by personal health sensor devices.

19. The system of claim 18, wherein the wearable device associated with each user of the plurality of users of the population comprises a personal health sensor device.

20. The system of claim 10, wherein the instructions are executable by the at least one processor to cause the at least one processor to perform operations further comprising: generating multiple training datasets over a plurality of iterations.

21. A non-transitory computer-readable storage media encoded with instructions executable by one or more processors to cause the at least one processor to perform operations comprising:
(a) identifying, based at least in part on one or more demographics of a target user, a population from a larger group of users, wherein the population comprises one or more digital twins of the target user, and wherein the population is characterized by having a common demographic;
(b) accessing, by a machine learning system, a set of data records for a plurality of users of the population, the data records representative of physical statistics measured for each user of the plurality of users of the population over a time period, wherein the physical statistics for each user of the plurality of users of the population are measured using a wearable device associated with each user of the plurality of users of the population;
(c) for each data record of a subset of data records:
(i) identifying, by the machine learning system, a portion of the time period corresponding to missing data, and
(ii) generating, by the machine learning system, a masked data record by masking a portion of an additional data record of the set of data records corresponding to the identified portion of the time period, to resemble a pattern of missing data from the set of data records, wherein the pattern of missing data corresponds to periods of disuse or deactivation of the wearable device associated with each user of the plurality of users of the population;
(d) generating, by the machine learning system, a training dataset comprising both of at least the portion of the additional data record and the corresponding generated masked data record for each data record of the subset of the set of data records;
(e) training, by the machine learning system, a machine learning model using the generated training dataset, the machine learning model configured to predict, for a received data record comprising masked data, imputed data corresponding to data of the received data record obscured based on the masked data;
(f) generating, by the machine learning system, a plurality of learned representations, wherein the plurality of learned representations are associated with the prediction of the imputed data as a result of the imputation of the masked data in the pattern of missing data; and
(g) fine-tuning, by the machine learning machine learning system, a learned representation of the plurality of learned representations to a downstream machine learning task, wherein the downstream machine learning task comprises processing a set of data records from a wearable device associated with the target user, thereby generating complete data for the target user.

22. A computer-implemented method of training a machine learning model to generate inferences from wearable sensor data, comprising:
(a) identifying, based at least in part on one or more demographics of a target user, a population from a larger group of users, wherein the population comprises one or more digital twins of the target user, and wherein the population is characterized by having a common demographic;
(b) retrieving a first set of wearable sensor data for each subject of a plurality of subjects of the population, wherein the first set of wearable sensor data for each subject of the plurality of subjects of the population is measured using a wearable device associated with each subject of the plurality of subjects of the population;
(c) selectively masking portions of at least a subset of the first set of wearable sensor data, wherein the masked portions of at least the subset of the first set of wearable sensor data are associated with periods of missing data and wherein the masking of the portions of at least the subset of the first set of the wearable sensor data causes the portions of at least the subset of the first set of the wearable sensor data to resemble a pattern of missing data from the set of data records, wherein the pattern of missing data corresponds to periods of disuse or deactivation of the wearable device associated with each user of the plurality of users of the population;
(d) creating a training set comprising at least the subset of the first set of wearable sensor data;
(e) training the machine learning model to impute data to the masked portions of at least the subset of the first set of wearable sensor data, thereby producing at least one learned representation from the training; and
(f) fine-tuning the at least one learned representation by using the machine learning model to a downstream machine learning task, wherein the downstream machine learning task comprises processing a second set of wearable sensor data from a wearable device associated with the target user, thereby generating complete data for the target user.

23. The method of claim 22, wherein the downstream machine learning task is imputation, regression, segmentation, or classification.

24. The method of claim 22, wherein the machine learning model comprises an attention mechanism.

25. The method of claim 24, wherein the attention mechanism is a multi-head attention mechanism.

26. The method of claim 22, wherein at least a portion of the first wearable sensor data is synthetically generated, wherein synthetically generating the at least the portion of the first wearable sensor data comprises:

(i) providing a set of time series wearable sensor data;
(ii) generating a plurality of embeddings from the time series wearable data, wherein an embedding of the plurality of embeddings comprises a sequence of values, wherein a value of the sequence of values is associated with a position of a set of positions; and
(iii) predicting a value for a position of the set of positions not associated with a value of the sequence of values by processing the plurality of embeddings with a second machine learning model, wherein the second machine learning model comprises an attention mechanism, wherein at least a portion of an attention weight matrix generated from processing the plurality of embeddings is masked.

27. The method of claim 26, wherein the set of positions comprises a set of positions in time, and wherein a position in time of the set of positions in time corresponds to a future position in time.

28. The method of claim 26, wherein the set of positions comprises a set of positions in time, and wherein a position in time of the set of positions in time corresponds to a masked position in time.

29. The method of claim 1, wherein the common demographic is a common health condition.

30. The method of claim 1, wherein the downstream machine learning task further comprises: predicting onset of a health condition for the target user based at least in part on the complete data for the target user.

* * * * *